(12) United States Patent
Lash et al.

(10) Patent No.: US 9,706,954 B1
(45) Date of Patent: *Jul. 18, 2017

(54) TISSUE OXIMETER INTRAOPERATIVE SENSOR

(71) Applicant: ViOptix Inc., Fremont, CA (US)

(72) Inventors: Robert E. Lash, Redwood City, CA (US); Scott Janis, San Francisco, CA (US); Darius Eghbal, Oakland, CA (US)

(73) Assignee: ViOptix, Inc., Newark, CA (US)

( * ) Notice: Subject to any disclaimer, the term of this patent is extended or adjusted under 35 U.S.C. 154(b) by 13 days.

This patent is subject to a terminal disclaimer.

(21) Appl. No.: 15/168,836

(22) Filed: May 31, 2016

Related U.S. Application Data

(63) Continuation of application No. 14/746,736, filed on Jun. 22, 2015, now Pat. No. 9,351,686, which is a continuation of application No. 14/017,021, filed on Sep. 3, 2013, now Pat. No. 9,060,720, which is a continuation of application No. 13/653,257, filed on Oct. 16, 2012, now Pat. No. 8,527,022, which is a (Continued)

(51) Int. Cl.
*A61B 5/1455* (2006.01)
*A61B 5/00* (2006.01)
*A61B 5/024* (2006.01)

(52) U.S. Cl.
CPC ...... *A61B 5/14552* (2013.01); *A61B 5/02427* (2013.01); *A61B 5/6843* (2013.01); *A61B 5/72* (2013.01); *A61B 5/742* (2013.01); *A61B 2560/0214* (2013.01); *A61B 2562/0247* (2013.01)

(58) Field of Classification Search
CPC ..... A61B 5/6843; A61B 5/14522; A61B 5/72; A61B 5/742; A61B 5/1455; A61B 2560/0214; A61B 2560/0425; A61B 2562/0247; A61B 2562/222

See application file for complete search history.

(56) References Cited

U.S. PATENT DOCUMENTS

| 3,874,781 A | 4/1975 | Thiel |
| 4,408,353 A | 10/1983 | Bowen et al. |

(Continued)

FOREIGN PATENT DOCUMENTS

| EP | 0476596 | 3/1992 |
| EP | 0663591 A | 7/1995 |

(Continued)

OTHER PUBLICATIONS

Dennis M. Hueber et al., "New Optical Probe Designs for Absolute (Self-Calibrating) NIR Tissue Hemoglobin Measurements," Proceedings of Optical Tomography and Spectroscopy of Tissue III, 3597 SPIE 618, 618-631, (Jan. 1999).

(Continued)

*Primary Examiner* — W B Perkey
(74) *Attorney, Agent, or Firm* — Aka Chan LLP

(57) ABSTRACT

An oximeter probe includes sensor head with a probe face having one or more sensor structures to make measurements, a handle, and an elastic member connected between the handle and the base. A user can hold the handle while measurements are made and the elastic member permits the handle to flex relative to the sensor head with one or more sensor structures.

27 Claims, 12 Drawing Sheets

Related U.S. Application Data continuation of application No. 12/623,945, filed on Nov. 23, 2009, now Pat. No. 8,290,558.

(56) References Cited

U.S. PATENT DOCUMENTS

| | | | |
|---|---|---|---|
| 4,884,095 A | 11/1989 | Yamanouchi et al. | |
| 4,910,539 A | 3/1990 | Mathis et al. | |
| 5,031,984 A | 7/1991 | Eide et al. | |
| 5,088,493 A | 2/1992 | Giannini et al. | |
| 5,212,748 A | 5/1993 | Curtiss et al. | |
| 5,224,478 A | 7/1993 | Sakai et al. | |
| 5,339,375 A | 8/1994 | Kerns | |
| 5,400,421 A | 3/1995 | Takahashi | |
| 5,548,672 A | 8/1996 | Hattori et al. | |
| 5,584,296 A | 12/1996 | Cui et al. | |
| 5,754,716 A | 5/1998 | Kim et al. | |
| 5,879,294 A | 3/1999 | Anderson et al. | |
| 5,978,534 A | 11/1999 | O'Rourke et al. | |
| 6,078,833 A | 6/2000 | Hueber | |
| 6,282,339 B1 | 8/2001 | Zheng | |
| 6,285,904 B1 | 9/2001 | Weber et al. | |
| 6,424,774 B1 | 7/2002 | Takeda et al. | |
| 6,487,343 B1 | 11/2002 | Lewandowski et al. | |
| 6,549,284 B1 | 4/2003 | Boas et al. | |
| 6,587,703 B2 | 7/2003 | Cheng et al. | |
| 6,597,931 B1 | 7/2003 | Cheng et al. | |
| 6,708,048 B1 | 3/2004 | Chance | |
| 6,859,658 B1 | 2/2005 | Krug | |
| 6,863,656 B2 | 3/2005 | Lurie | |
| 6,892,006 B2 | 5/2005 | Lewandowski et al. | |
| 6,909,912 B2 | 6/2005 | Melker | |
| 7,254,427 B2 | 8/2007 | Cho et al. | |
| 8,290,558 B1 | 10/2012 | Lash et al. | |
| 8,527,022 B1 * | 9/2013 | Lash | A61B 5/6843 600/323 |
| 9,060,720 B1 * | 6/2015 | Lash | A61B 5/6843 |
| 9,351,686 B1 * | 5/2016 | Lash | A61B 5/6843 |
| 2003/0144583 A1 | 7/2003 | Cheng et al. | |
| 2004/0111016 A1 | 6/2004 | Casscells et al. | |
| 2007/0016079 A1 | 1/2007 | Freeman et al. | |
| 2007/0024946 A1 | 2/2007 | Panasyuk et al. | |
| 2007/0038042 A1 | 2/2007 | Freeman et al. | |
| 2007/0249913 A1 | 10/2007 | Freeman et al. | |
| 2007/0260131 A1 | 11/2007 | Chin | |
| 2009/0171224 A1 | 7/2009 | Jochim et al. | |
| 2009/0326354 A1 | 12/2009 | Mao et al. | |

FOREIGN PATENT DOCUMENTS

| | | |
|---|---|---|
| EP | 0800099 | 8/1997 |
| EP | 0816829 | 7/1998 |
| EP | 1518494 A | 3/2005 |
| GB | 1386734 | 3/1975 |
| GB | 1558643 | 9/1980 |
| WO | 96/41566 A | 12/1996 |
| WO | 98/22018 A | 5/1998 |
| WO | 00/28887 A | 5/2000 |

OTHER PUBLICATIONS

De Myers et al., "Noninvasive Method for Measuring Local Hemoglobin Oxygen Saturation in Tissue Using Wide Gap Second Derivative Near-Infared Spectroscopy," Level1Diet, 10(3) J Biomed Opt. 034017, (May-Jun. 2005), at http://www.level1diet.com/893768_id (last visited Mar. 25, 2008).

Dustin Kasel, "Tissue Oxygen Saturation as a Non-Invasive Measurement for Cardiac Output," (Nov. 18, 2007), at http://biomedprojects.org/home/projects/papers/tissue-oxygen-saturation-measurement-as-a-non-invasive-alternative-to-cardiac-output-1 (last visited Mar 25, 2008).

AJ Comerota et al., "Tissue (muscle) Oxygen Saturation (StO2): A New Measure of Symptomatic Lower-Extremity Arterial Disease," 38(4) J Vasc Surg. 724, 724-29, (Oct. 2003), at http://www.ncbi.nlm.nih.gov/pubmed/14560221?dopt=Abstract (last visited Mar. 25, 2008).

Rudi Kragelj et al., "Parameters of Postocclusive Reactive Hyperemia Measured by Near Infrared Spectroscopy in Patients with Peripheral Vascular Disease and in Healthy Volunteers," 29(4) Annals of Biomedical Engineering 311, 311-320 (2001).

* cited by examiner

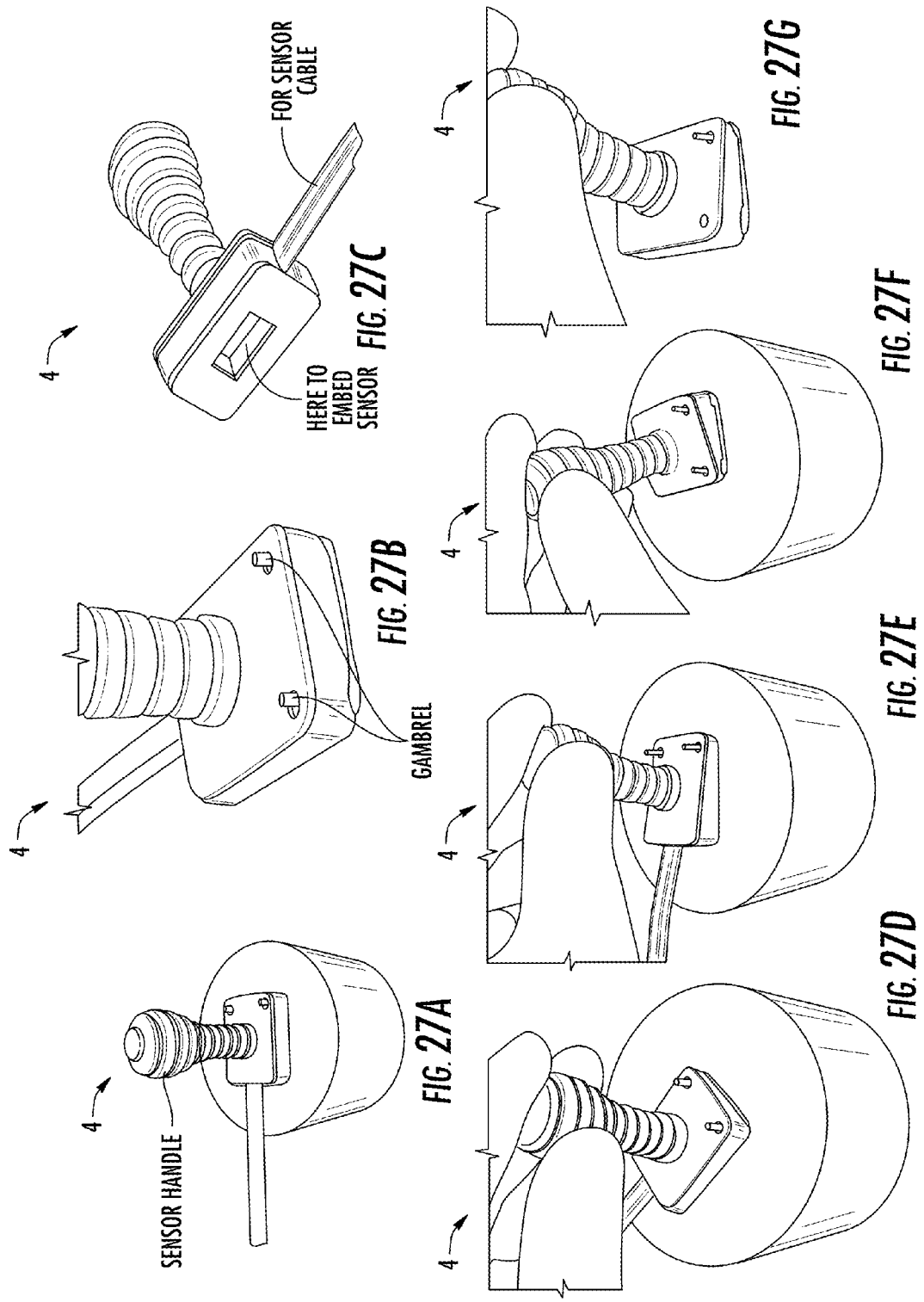

TISSUE OXIMETER INTRAOPERATIVE SENSOR

CROSS-REFERENCE TO RELATED APPLICATIONS

This patent application is a continuation of U.S. patent application Ser. No. 14/746,736, filed Jun. 22, 2015, issued as U.S. Pat. No. 9,351,686 on May 31, 2016, which is a continuation of U.S. patent application Ser. No. 14/017,021, filed Sep. 3, 2013, issued as U.S. Pat. No. 9,060,720 on Jun. 23, 2015, which is a continuation of U.S. patent application Ser. No. 13/653,257, filed Oct. 16, 2012, issued as U.S. Pat. No. 8,527,022 on Sep. 3, 2013, which is a continuation of U.S. patent application Ser. No. 12/623,945, filed Nov. 23, 2009, issued as U.S. Pat. No. 8,290,558 on Oct. 16, 2012. These applications are incorporated by reference along with all other references cited in this application.

BACKGROUND OF THE INVENTION

This invention relates to the field of medical devices, and more specifically to an oximeter tool with a pressure limiting mechanism.

Medical devices play a critical role in medicine. Users, such as doctors, use medical devices to save lives and improve the well-being and quality of life for patients. Numerous advancements in medical devices have been made over the last several decades. Some examples include the operating microscope which allows surgeons to see and operate on small tissue parts and the endoscope which allows for minimally invasive exams and procedures.

Other examples of medical devices include sensors which monitor patients. Such sensors make measurements such as oxygen saturation of tissue, pulse, blood pressure, temperature, and other physiological measurements.

In some cases, these sensors are placed on or near the tissue to be measured, such as by using an adhesive to secure the sensor to the tissue. In other cases, it may not be possible or it may be difficult to use an adhesive. In these cases, the user may manually hold the sensor against the tissue. It can be difficult for the user to maintain a proper pressure or a range of proper pressures of the sensor against the tissue so that the sensor can make accurate measurements. For example, over the course of the monitoring the user may become tired or fatigued. This may lead the user to press the sensor against the tissue using an excessive level of force. This can lead to undesirable changes in the tissue such as a disruption of the local perfusion which in turn may lead to inaccurate measurements.

Therefore, there is a need for a new and improved oximeter tool with a pressure limiting mechanism.

BRIEF SUMMARY OF THE INVENTION

An oximeter probe includes sensor head with a probe face having one or more sensor structures to make measurements, a handle, and an elastic member connected between the handle and the base. A user can hold the handle while measurements are made and the elastic member permits the handle to flex relative to the sensor head with one or more sensor structures.

In a specific implementation, an oximeter device includes a base portion to face a tissue to be measured, at least one sensor opening formed on a bottom surface of the base portion, a handle, a spring, connected between the base portion and the handle, a pair of limit stops including an upper limit stop and a lower limit stop, and a stop pin. The stop pin is received between the upper and lower limit stops. The pair of limit stops is fixed relative to one of the handle or base portion. The stop pin is fixed relative to another of the handle or base portion. The spring urges the upper limit stop and the stop pin apart to create a first gap between the upper limit stop and the stop pin. The lower limit stop may contact the stop pin to limit a travel of the handle such as preventing the handle from springing backwards.

In an implementation, the spring is connected at a first end of the handle and a portion of the handle extending from the first end to a second end of the handle, opposite the first end, extends without projecting over the at least one sensor opening.

A height of the base portion between the bottom surface and a top surface of the base portion, opposite the bottom surface, may be about 6 millimeters or less. The spring may include plastic.

In a specific implementation, the pair of limit stops is closer to the at least one sensor opening than the spring. In another implementation, the spring is closer to the at least one sensor opening than the pair of limit stops.

In a specific implementation, the upper limit stop and the stop pin touch to close the first gap when a force applied to the handle exceeds a threshold value. The pair of limit stops may be contained within a recess of the handle. In this implementation, the upper limit stop is at a first end of the recess. The lower limit stop is at a second end of the recess, opposite the first end.

In a specific implementation, the at least one sensor opening is contained within a sensor unit. In this specific implementation, the sensor unit includes a first source structure, a second source structure, a first detector structure including optical fiber, and a second detector structure including optical fiber. A first distance is between the first source structure and the first detector structure. A second distance is between the first source structure and the second detector structure. A third distance is between the second source structure and the first detector structure. A fourth distance is between the second source structure and the second detector structure.

The first distance is not equal to the second, third, and fourth distances. The second distance is not equal to the third and fourth distances. The third distance is not equal to the fourth distance.

A first end of the handle may be supported by the spring and a second end of the handle, opposite the first end, may be unsupported so that there is a second gap below the second end of the handle.

In a specific implementation, a method of making an oximeter device includes providing a single piece of material including a base portion, a spring portion, and a handle portion. Attaching an oximeter sensor to a bottom surface of the base portion. Routing a cable of the oximeter sensor through a channel in the handle portion. And attaching a pad to the bottom surface of the base portion.

In another implementation, a method of making the device includes molding the plastic handle, inserting the sensor head and cable through the handle, gluing the back of the sensor head to the handle, applying an adhesive foam pad (e.g., one side of the foam pad is pre-coated with an adhesive and the other side of the foam is pre-covered with an opaque adhesive light-shield film) such that the foam pad surrounds the sensor head and sticks to the handle.

The method may further include forming a set of alternating ridges and valleys on the handle portion. A thickness of a ridge may be equal to a thickness of a valley. The ridges and valleys can help to improve grip, lighten the weight, or both. The ridges and valleys can help to reduce manufacturing costs. The single piece of material may include plastic (e.g., polypropylene, polyethylene, or polyurethane).

The pad may include foam. The pad may be referred to as a light shield pad. In a specific implementation, the pad is compressible. One may see the pad starts to be partially compressed when the force is in the order of about 0.1 pounds or less (i.e., 45 grams or less). In this specific implementation, the sensor head is not compressible and is equal to or greater than the thickness of the foam pad which surrounds or at least partially surrounds the sensor head in a semi-annular horseshoe. Therefore, most of the applied force will be transmitted from the handle, through the spring, to the incompressible sensor head, and then into the contacting tissue.

In a specific implementation, the method further includes bending the spring portion and bringing the base and handle portion together to engage a stop pin of the base portion with a stop pin receiving region of the handle portion.

In a specific implementation, an oximeter device includes a base portion to face a tissue to be measured, at least one sensor structure on a bottom surface of the base portion, and a set of markings on a top surface of the base portion, opposite the bottom surface, to aid in aligning the at least one sensor structure on the tissue. There is a spring and a handle connected to the base portion through the spring. The spring permits the handle to flex relative to the at least one sensor structure on the bottom surface of the base portion.

The spring may be a living hinge and the base portion, handle, and living hinge may be molded as a single unit. A cross section of the living hinge may include a middle region between opposite end regions and a thickness of the living hinge may taper from the middle region towards the opposite end regions.

In a specific implementation, the set of markings includes a first arrow pointing towards a first side edge of the base portion, a second arrow pointing towards a second side edge of the base portion, opposite the first side edge, and a third arrow pointing towards a top edge of the base portion, between the first and second side edges.

In a specific implementation, the oximeter device further includes an extension to offset the handle from the base portion. A first end of the extension is connected to the base portion. A second end of the extension, opposite the first end, is connected to the spring. A bottom surface of the handle extends from the second end towards the first end and terminates before extending over the at least one sensor structure.

This tool or handle with an oximeter sensor head can be used during reconstructive microsurgical procedures where there is a need to be able to measure one or more regions of a flap intraoperatively. Some other applications include the real-time selection of perforator vessels by means of sequential clamping, mastectomy margin mapping, and confirmation of flap reperfusion prior to leaving the operating room to help reduce take-back rates.

Existing designs using adhesive pads are not ideally suited for intraoperative use due to exposure of the adhesive pad to blood and fluids in the intraoperative sterile field which can reduce the pads adhesion when later applied. In addition, the variation in applied pressure (which can alter the actual StO2 in a region of tissue) when holding the sensor head to the flap by hand is generally considerably greater than when the sensor head is adhesively applied, and thus a mechanism to reduce pressure variation is desirable when spot-check sensing. Therefore an optimized small patch sensor fixation system for intraoperative use is needed.

The tool may be used to noninvasively estimate the percent oxygen saturation (StO2) in a volume of tissue. This may be performed in medical environments including physician offices, hospitals, ambulatory care, and emergency medical services. The tool may be indicated for use in monitoring patients during circulatory or perfusion examinations of skeletal muscle or when there is a suspicion of compromised circulation.

In a specific implementation, a small patch sensor for use on flaps is integrated into a permanently affixed pressure control handpiece with light shield. The intraop sensor is provided as a sterile disposable. The tool is resistant to moisture. The sensor cable is routed through the tool to allow for cable strain resistance.

The tool may be used in the operating room environment, where strong operating room lighting is expected. In addition, it should be noted that the sensor and oximeter meets EMC emission requirements for preventing interference with standard operating room equipment. The tool is easy to use, and the sensor can be reliably positioned onto the flap with controlled pressure for stable StO2 readings. The tool is usable in operating room lighting conditions.

Typically, fully biocompatible medical-grade materials are used for the patient contacting portion of the sensor (or intraop sensor). In addition, electrical and laser hazard risks are mitigated in accordance with IEC-60601-1 (Medical Electrical Safety) and IEC60825-1 (Laser Safety) standards.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIGS. 27A-27G show a fourth alternative implementation of the tool in use.

DETAILED DESCRIPTION OF THE INVENTION

Figure 1:
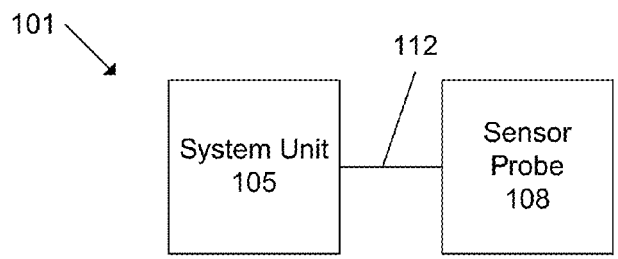
FIG. 1 shows a block diagram for measuring oxygen saturation of tissue in a patient.

FIG. 1 shows an oximeter system 101 for measuring oxygen saturation of tissue in a patient. The system includes a system unit 105 and a sensor probe 108, which is connected to the system unit via a wired connection 112. Connection 112 may be an electrical, optical, or another wired connection including any number of wires (e.g., one, two, three, four, five, six, or more wires or optical fibers), or any combination of these or other types of connections. In other implementations of the invention, however, connection 112 may be wireless such as via a radio frequency (RF) or infrared communication.

Typically, the system is used by placing the sensor probe in contact or close proximity to tissue (e.g., skin or nerve) at a site where an oxygen saturation or other related measurement is desired. The system unit causes an input signal to be emitted by the sensor probe into the tissue (e.g., human tissue). There may be multiple input signals, and these signals may have varying or different wavelengths. The input signal is transmitted into or through the tissue.

Then, after transmission through or reflection off the tissue, the signal is received at the sensor probe. This received signal is received and analyzed by the system unit. Based on the received signal, the system unit determines the oxygen saturation of the tissue and displays a value on a display of the system unit.

In an implementation, the system is a tissue oximeter, which can measure oxygen saturation without requiring a pulse or heart beat. A tissue oximeter of the invention is applicable to many areas of medicine and surgery including plastic surgery and spinal surgery. The tissue oximeter can make oxygen saturation measurements of tissue where there is no pulse; such tissue, for example, may have been separated from the body (e.g., a flap) and will be transplanted to another place in the body.

Aspects of the invention are also applicable to a pulse oximeter. In contrast to a tissue oximeter, a pulse oximeter requires a pulse in order to function. A pulse oximeter typically measures the absorbances of light due to the pulsing arterial blood.

There are various implementations of systems and techniques for measuring oxygen saturation such as discussed in U.S. Pat. Nos. 6,516,209, 6,587,703, 6,597,931, 6,735,458, 6,801,648, and 7,247,142. These patents are assigned to the same assignee as this patent application and are incorporated by reference.

Figure 2:
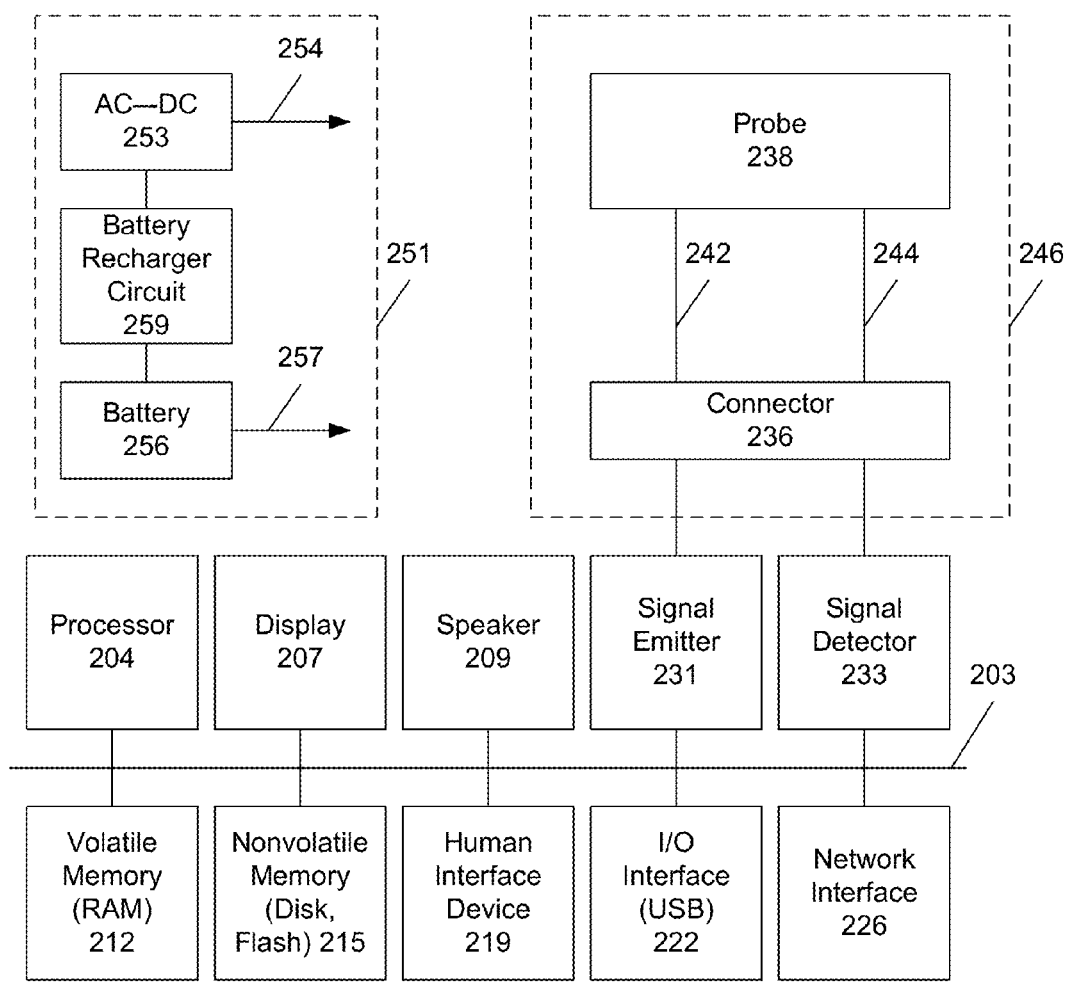
FIG. 2 shows in greater detail a specific implementation of the system of FIG. 1.

FIG. 2 shows greater detail of a specific implementation of the system of FIG. 1. The system includes a processor 204, display 207, speaker 209, signal emitter 231, signal detector 233, volatile memory 212, nonvolatile memory 215, human interface device or HID 219, I/O interface 222, and network interface 226. These components are housed within a system unit enclosure. Different implementations of the system may include any number of the components described, in any combination or configuration, and may also include other components not shown.

The components are linked together using a bus 203, which represents the system bus architecture of the system. Although this figure shows one bus that connects to each component, the busing is illustrative of any interconnection scheme serving to link the subsystems. For example, speaker 209 could be connected to the other subsystems through a port or have an internal direct connection to processor 204.

A sensor probe 246 of the system includes a probe 238 and connector 236. The probe is connected to the connector using wires 242 and 244. The connector removably connects the probe and its wires to the signal emitter and signal detectors in the system unit. There is one cable or set of cables 242 to connect to the signal emitter, and one cable or set of cables 244 to connect to the signal detector. In an implementation the cables are fiber optic cables, but in other implementations, the cables are electrical wires.

Signal emitter 231 is a light source that emits light at one or more specific wavelengths. In a specific implementation, two wavelengths of light (e.g., 690 nanometers and 830 nanometers) are used. In other implementations, other wavelengths of light may be used. The signal emitter is typically implemented using a laser diode or light emitting diode (LED). Signal detector 233 is typically a photodetector capable of detecting the light at the wavelengths produced by the signal emitter.

The connector may have a locking feature; e.g., insert connector, and then twist or screw to lock. If so, the connector is more securely held to the system unit and it will need to be unlocked before it can be removed. This will help prevent accidental removal of the probe.

The connector may also have a first keying feature, so that the connector can only be inserted into a connector receptacle of the system unit in one or more specific orientations. This will ensure that proper connections are made.

The connector may also have a second keying feature that provides an indication to the system unit which type of probe is attached. The system unit may handle making measurements for a number of different types of probes. When a probe is inserted, the system uses the second keying feature to determine which type of probe is connected to the system. Then the system can perform the appropriate functions, use the proper algorithms, or otherwise make adjustments in its operation for the specific probe type.

For example, when the system detects a cerebral probe is connected, the system uses cerebral probe algorithms and operation. When the system detects a thenar probe is connected, the system uses thenar probe algorithms and operation. A system can handle any number of different types of probes. There may be different probes for measuring different parts of the body, or different sizes or versions of a probe for measuring a part of the body (e.g., three different thenar probe models).

With the second keying feature, the system will be able to distinguish between the different probes. The second keying feature can use any type of coding system to represent each probe including binary coding. For example, for a probe, there are four second keying inputs, each of which can be a logic 0 or 1. With four second keying inputs, the system will be able to distinguish between sixteen different probes.

Typically, probe 246 is a handheld tool and a user moves the probe from one point to another to make measurements. However, in some applications, probe 246 is part of an endoscopic instrument or robotic instrument, or both. For example, the probe is moved or operated using a guiding interface, which may or may not include haptic technology.

In various implementations, the system is powered using a wall outlet or battery powered, or both. Block 251 shows a power block of the system having both AC and battery power options. In an implementation, the system includes an AC-DC converter 253. The converter takes AC power from a wall socket, converts AC power to DC power, and the DC output is connected to the components of the system needing power (indicated by an arrow 254). In an implementation, the system is battery operated. The DC output of a battery 256 is connected to the components of the system needing power (indicated by an arrow 257). The battery is recharged using a recharger circuit 259, which received DC power from an AC-DC converter. The AC-DC converter and recharger circuit may be combined into a single circuit.

The nonvolatile memory may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), flash and other nonvolatile solid-state storage (e.g., USB flash drive), battery-backed-up volatile memory, tape storage, reader, and other similar media, and combinations of these.

The processor may include multiple processors or a multicore processor, which may permit parallel processing of information. Further, the system may also be part of a distributed environment. In a distributed environment, individual systems are connected to a network and are available to lend resources to another system in the network as needed. For example, a single system unit may be used to collect results from numerous sensor probes at different locations.

Aspects of the invention may include software executable code or firmware (e.g., code stored in a read only memory or ROM chip). The software executable code or firmware may embody algorithms used in making oxygen saturation measurements of the tissue. The software executable code or firmware may include code to implement a user interface by which a user uses the system, displays results on the display, and selects or specifies parameters that affect the operation of the system.

Further, a computer-implemented or computer-executable version of the invention may be embodied using, stored on, or associated with a computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on a mass storage device. Source code of the software of the present invention may also be stored or reside on a mass storage device (e.g., hard disk, magnetic disk, tape, or CD-ROM). As a further example, code of the invention may be transmitted via wires, radio waves, or through a network such as the Internet. Firmware may be stored in a ROM of the system.

Computer software products may be written in any of various suitable programming languages, such as C, C++, C#, Pascal, Fortran, Perl, Matlab (from MathWorks, www.mathworks.com), SAS, SPSS, JavaScript, AJAX, and Java. The computer software product may be an independent application with data input and data display modules. Alternatively, the computer software products may be classes that may be instantiated as distributed objects. The computer software products may also be component software such as Java Beans (from Sun Microsystems) or Enterprise Java Beans (EJB from Sun Microsystems).

An operating system for the system may be one of the Microsoft Windows® family of operating systems (e.g., Windows 95, 98, Me, Windows NT, Windows 2000, Windows XP, Windows XP x64 Edition, Windows Vista, Windows CE, Windows Mobile), Linux, HP-UX, UNIX, Sun OS, Solaris, Mac OS X, Alpha OS, AIX, IRIX32, or IRIX64. Microsoft Windows is a trademark of Microsoft Corporation. Other operating systems may be used, including custom and proprietary operating systems.

Furthermore, the system may be connected to a network and may interface to other systems using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, and 802.11n, just to name a few examples). For example, signals from a system may be transferred, at least in part, wirelessly to components or other systems or computers.

In an embodiment, through a Web browser or other interface executing on a computer workstation system or other device (e.g., laptop computer, smartphone, or personal digital assistant), a user accesses a system of the invention through a network such as the Internet. The user will be able to see the data being gathered by the machine. Access may be through the World Wide Web (WWW). The Web browser is used to download Web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 3A:
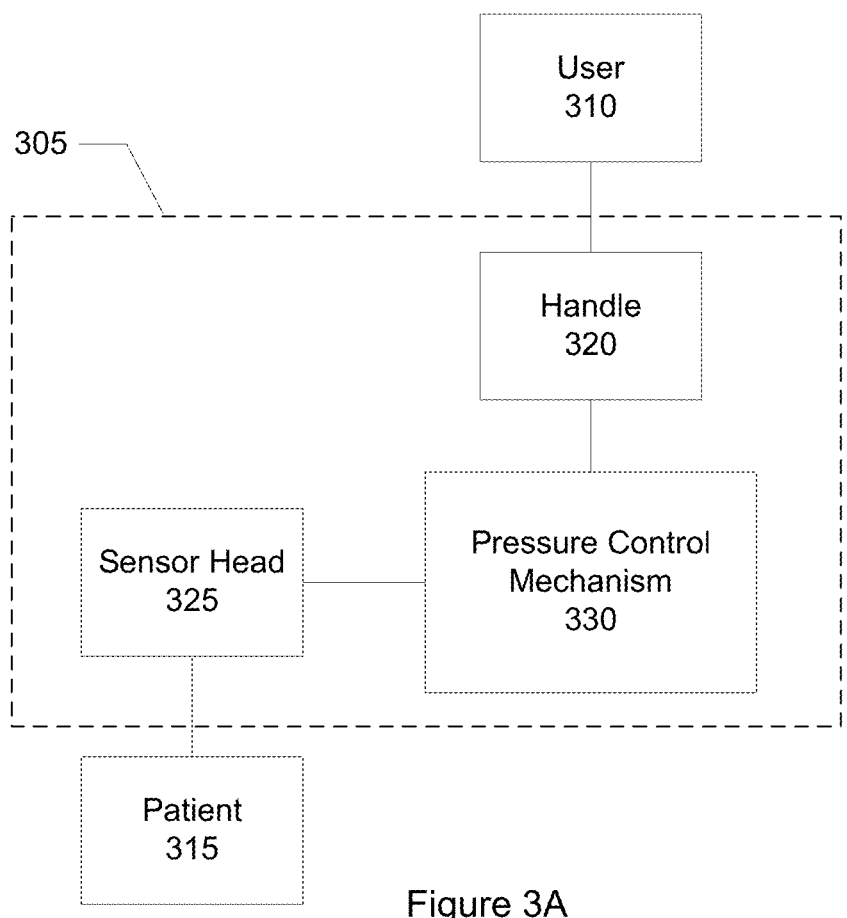
FIG. 3A shows a block diagram of a tool having a sensor, pressure control mechanism, and handle.

FIG. 3A shows a block diagram of an implementation of the invention which can facilitate accurate measurements of oxygen saturation of tissue by ensuring that the sensor head is being properly held against the tissue. A probe or tool 305 is used by a user 310 to make measurements, such as oxygen saturation measurements, of a patient (or tissue) 315. The tool may be referred to as a sensor unit holder. A typical user is a physician, surgeon, doctor, nurse, technician, or other health care professional. The patient is typically a human patient who is undergoing a surgical procedure such as a free tissue or free flap transfer reconstruction. However, the tool may be used in nonsurgical procedures. The tool may be used with nonhuman patients such as animals (e.g., pigs, dogs, cats, horses, cows, rabbits, rats, and monkeys).

The tool includes a handle 320 so that the tool can be held, a sensor head or unit 325, and a pressure control mechanism 330 between the handle and the sensor head. The pressure control mechanism helps to ensure that the user does not press the sensor head too tightly against the tissue via the handle. The pressure control mechanism can help ensure that a proper pressure or force or a range of proper pressures or forces of the sensor head against the tissue is maintained as measurements are made.

In some cases, it can be difficult to attach the sensor unit to the tissue to be monitored such as by using an adhesive pad or tape. Fluids such as blood around the surgical site or intraoperative sterile field can reduce the adhesion of the pad. The sensor may then slip or fall off the tissue. However, simply holding the sensor unit against the tissue may result in inaccurate measurements because the user may not be able to hold the sensor unit in a steady position against the tissue. Variations in pressure of the sensor head against the tissue such as pressing the sensor head too tightly or too lightly against the tissue can result in incorrect measurements. For example, too much pressure on the tissue can disturb the local perfusion and alter the measurements (e.g., alter the tissue's actual oxygen saturation). This pressure control mechanism can help reduce the pressure variation.

In a specific implementation, the sensor head is part of an oximeter system for measuring oxygen saturation of tissue in a patient such as the system shown in FIGS. 1-2 and discussed above. In this specific implementation, the sensor head includes an arrangement of source structures which transmit radiation or light into the tissue and an arrangement of detector structures which receive the transmitted light or a portion of the transmitted light so that oxygen saturation measurements can be determined. Some examples of source and detector structure arrangements are shown in FIGS. 15-22. This tool can be used during reconstructive microsurgical procedures where there is a need to be able to measure one or more regions of a flap intraoperatively, i.e., during the surgery.

One of skill in the art will recognize that any sensor head may used with this tool to make any measurement where it is desirable to ensure that the sensor head is not pressed too tightly against the tissue. Some examples of other measurements that may be made with other types of sensor heads include temperature, blood pressure, chemical concentration, or flow measurements, or any other physiological measurements.

In a specific implementation, the pressure control mechanism is a mechanical arrangement or design. The mechanical arrangement may include a spring (i.e., an elastic body or device that recovers its original shape when released after being distorted). In this specific implementation, the pressure control mechanism is passive and does not include electrical components (e.g., electrical wiring and strain gauges) to help the user maintain the proper pressure (or a range of proper pressures) of the sensor head against the tissue.

The absence of electrical components in the pressure control mechanism allows the tool to be manufactured economically or at a lower cost as compared to other tools which may include electrical components to sense pressure or force. In this specific implementation, the tool is designed to be disposable, such as after one use. In another implementation, the pressure control mechanism instead or additionally includes electrical components. For example, an electrically operated pressure sensor may be placed on the sensor head to detect the pressure being applied to the tissue by the sensor head. A pressure sensor may be positioned between the tissue and the sensor head. A pressure sensor may be positioned between the tissue and a base of the tool. Components of the pressure control mechanism may include electrical wiring, strain gauges, semiconductor strain gauges, piezoresistors, or combinations of these.

In a specific implementation, the tool including the sensor head or sensor unit, cable or wires, and connector are packaged as a probe unit in a package that is sterile. The probe unit is detachable from the console after use and may be disposed. The user can then open a new package containing a new probe unit. The package may be opened at the time of actual use or near the time of actual use so as to not contaminate the probe unit. The user can then connect this new probe unit that is sterile to the console to begin monitoring. This disposable feature helps to ensure a sterile field around the patient.

Figure 3B:
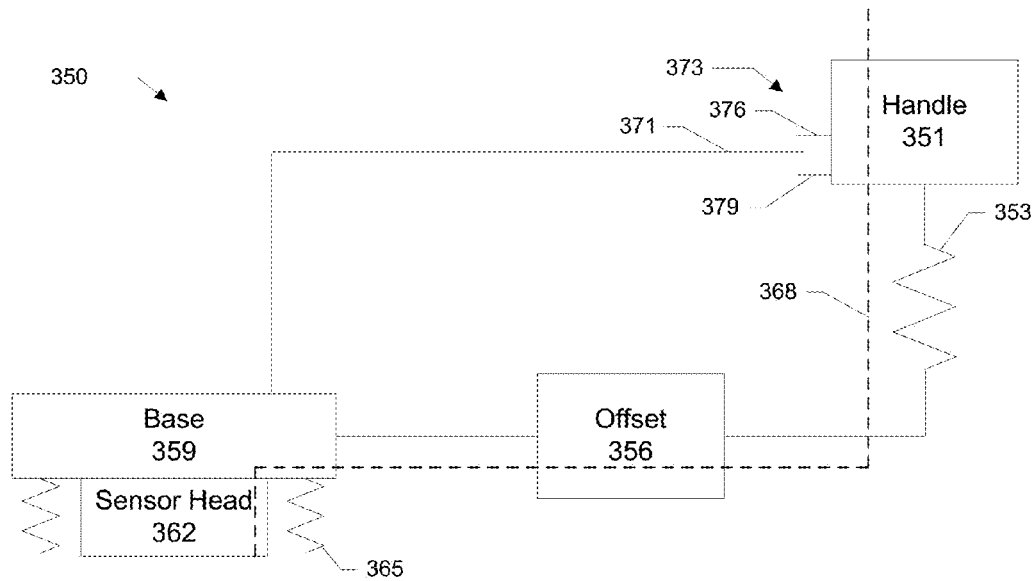
FIG. 3B shows a schematic diagram of a specific implementation of the tool.

FIG. 3B shows a schematic diagram of a specific implementation of a tool 350. The tool includes a handle 351 connected to a first spring 353 connected to an offset 356 connected to a base 359 connected to a sensor head 362. Second springs 365 (such as a resilient foam pad), in parallel, are connected to the base and at least partially surround or entirely surround the sensor head. A cable 368 runs from the sensor head, along the base, offset, and first spring and into and through the handle where the cable connects to a system unit such as the system unit shown in FIG. 1. The tool further includes a stop pin 371 and a limit region 373 having a pair of limit stops, i.e., upper limit stop 376 and lower limit stop 379.

In brief, a sequence of operation for the tool is:

1. A user holds the handle and positions the sensor head or sensor unit to face a tissue to be measured.

2. The user applies a force or moment to the handle against a bias force of the spring and in a direction towards the tissue so that the sensor unit is held against the tissue.

3. As the user applies the force the spring flexes as the handle moves, rotates, pivots, or travels towards the tissue and the sensor head exerts a force or pressure on the tissue as result of the applied force at the handle. The user can gauge or estimate the pressure being applied to the tissue by observing the position of the stop pin relative to the pair of limit stops. For example, in a specific implementation, the tool is designed or calibrated so that the upper limit stop indicates that a desired maximum pressure to apply to the tissue via the tool has been exceeded.

Thus, the user can observe the distance between the upper limit stop and the stop pin. So long as the user maintains a gap between the upper limit stop and the stop pin, the user will know that an excess level of pressure or force is not being applied to the tissue.

In a specific implementation, the cable includes one or more optical fibers or optical fiber bundles. The optical fibers transmit light from the system console to sensor openings (i.e., source sensor openings) on the sensor head or base and into the tissue. Light from the tissue is received by sensor openings (i.e., detector sensor openings) on the sensor head or base and is transmitted back to the system console. Ends of the optical fiber are connected to the sensor openings and opposite ends of the optical fiber are connected to light sources or detectors (e.g., photodiodes) at the system console. In this specific implementation, the cable does not include electrical wires.

In other implementations, the cable includes electrical wires. The cable may include electrical wires and optical fiber. The cable may include electrical wires and no optical fiber. For example, in a specific implementation, a light source such as a light emitting diode is at the sensor unit. The cable may then include an electrical wire to supply power to the light emitting diode. As another example, a detector such as a photodiode or photodetector is at the sensor unit. The cable may then include an electrical wire to transmit an electrical signal produced by the photodiode back to the system console.

The offset may be designed to be a rigid member relative to the springs. The offset allows the handle to be positioned away from the base. In other words, in this specific implementation, the handle is not directly above the base. Rather, the handle is off to a side of the base or is offset (i.e., laterally offset) in a horizontal direction from a position vertically above the base. The handle is positioned in a direction upwardly and obliquely from the base.

In an implementation, a line coincident with a direction of gravity passes through the base (i.e., passes through the sensor unit or passes through a sensor opening or sensor structure of the sensor unit). A second line extends in a direction perpendicular to the first line until the second line intersects a surface of the handle. The first line does not pass through the handle. A distance between the first line and the handle may be represented by the offset. The amount of offset may be the length of the second line. The offset amount can range from about 1 millimeter to about 100 millimeters. This includes, for example, 10, 15, 20, 25, 30, 35, 40, 50, 60, 70, 80, 90, or 99.9 millimeters. The amount can be greater than 100 millimeters or less than 1 millimeter.

In another implementation, an outline encircling the sensor openings defines a boundary line. A boundary region bounded by the boundary line extends in a vertical direction or in a direction perpendicular to a plane in which the sensor openings lie. In this specific implementation, the handle is offset from the sensor openings such that the handle does not intersect the boundary region.

The absence of a handle or other structure above the base or sensor unit eliminates or minimizes interference by the handle thus permitting the sensor unit to, for example, slide between two tissues to make measurements.

Further, the specific amount of offset can be used individually or in combination with other design variables to determine the pressure or force at the tissue in response to an applied force or moment at the handle. For example, the offset may be considered as a moment or lever arm. The first spring can be a linear spring or a torsional spring. The force of a spring, such as a linear spring, is given by:

$$F = -kx \qquad (1)$$

where x is the displacement of the end of the spring and k is the spring constant. Similarly, the torque of a torsional or rotational spring is:

$$t = -k\theta \qquad (2)$$

where θ is the angle of twist of the spring from its equilibrium position in radians and k is the spring constant (i.e., torsion coefficient, torsion elastic modulus, or rate). These equations may be referred to as Hooke's Law or Hooke's Law of Elasticity. Hooke's Law is an approximation that states the extension of a spring is in direct proportion with the load added to it as long as this load does not exceed the elastic limit. Above a certain stress or force which may be referred to as the elastic limit or yield strength of an elastic material, the solid (e.g., the spring) may deform irreversibly, exhibiting plasticity. Generally, the forces discussed in this application applied to the spring to bend the spring will be within the elastic range (not plastic range) of the spring. In other implementations, the forces will exceed the elastic range of the spring.

The torque or moment of a force with respect to a point is:

$$m = Fd \qquad (3)$$

where F is the force applied at a distance d from the point. In an implementation, distance d is a length of the offset or lever arm.

As one of skill in the art will recognize, variables such as the spring constant, length of the lever arm, distance between the upper and lower limits, number of springs, arrangement of springs (e.g., springs in parallel and springs in series), and combinations of these can be varied to produce a desired pressure at the sensor unit in response to an applied force or moment at the handle. The tool can be designed so that the pressure or force at the tissue will be less than, equal to, or greater than the force applied at the handle.

Factors that may contribute to the spring constant include the spring dimensions such as the spring's length, width, or thickness, shape or cross-sectional shape of the spring which can affect a moment of inertia, the material that the spring is made of (e.g. plastic or metal), or combinations of these.

An implementation may include two or more springs in series (e.g., springs linked end-to-end), two or more springs in parallel (e.g. springs side-by-side), or a combination of springs in series and springs in parallel. For springs in parallel, the equivalent spring constant of the combination is a sum of the spring constants of each individual spring. For springs in series, to find the equivalent spring constant of the combination, add the reciprocals of the spring constants of each individual spring and take the reciprocal of the sum.

First spring 353 may be on either or both sides of the offset. In this specific implementation, first spring 353 is on a first side (e.g., right-hand side) of the offset. The offset is between the base and the first spring. In another implementation, the first spring is on a second side (e.g., left-hand side) of the offset, opposite the first side. The first spring is between the base and the offset. In another implementation, there is a spring on the first side of the offset and another spring on the second side of the offset.

In other implementations, the handle is not offset from the base. That is, the handle is above or directly above the base. An example of such an implementation is alternative design four shown in FIGS. 25-27G.

Figure 4:
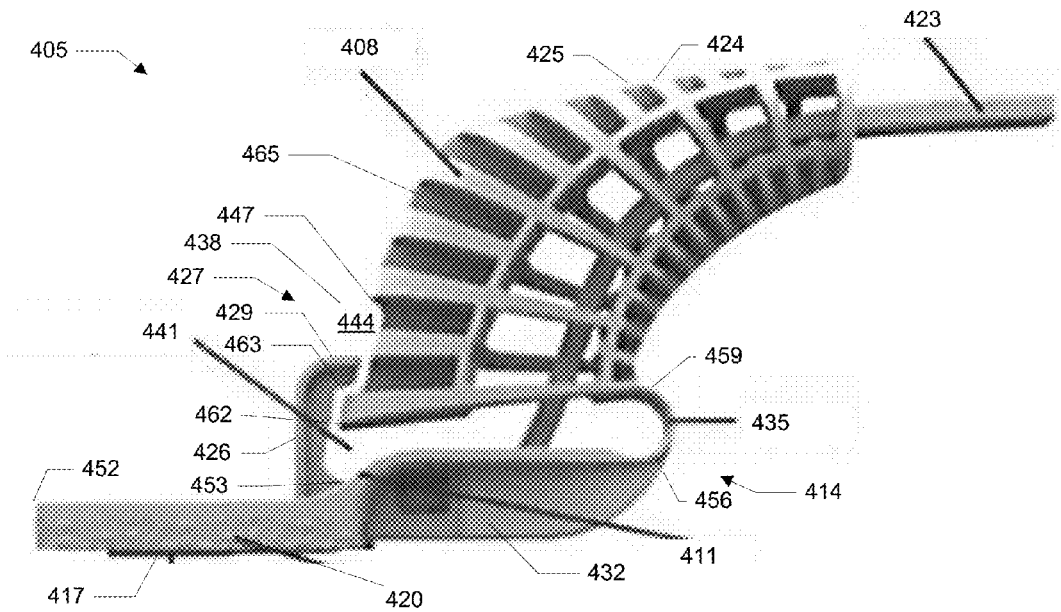
FIG. 4 shows a side view of a specific implementation of the tool of FIG. 3B.

FIG. 4 shows a side view of a specific implementation of a tool 405. The tool includes a handle 408, a base 411, and a pressure control mechanism 414 between the handle and the base. A sensor unit 417 and a pad or foam pad 420 at least partially surrounding the sensor unit are attached to a bottom surface of the base. A cable 423 is connected to the sensor unit and is routed through the tool. The handle includes a set of ridges 424 which alternate with a set of valleys 425.

The pressure control mechanism includes a gauge 427 and a spring 435. The gauge includes a stop or stop pin 429 and a recess or limit region 438 that has a pair of limit stops—an upper limit stop 447 and a lower limit stop 463. The stop pin is engaged or received between the upper and lower limit stops.

The spring is connected between the base and the handle so that there is a first gap 441 formed between the handle and an extension 432. A second gap 444 is formed between upper limit stop 447 at a top end of the recess and the stop pin. The second gap may be referred to as a pressure limiting gap. The stop pin engages the recess or is received between the upper and lower limit stops.

In this specific implementation, when the user applies a force or moment to the handle, the handle rotates or pivots downward about the spring and towards the tissue, closing the first and second gaps. That is, the upper limit stop moves towards the stop pin. The user can gauge the pressure being applied to the tissue by the tool by observing the distance or size of the second gap between the upper limit stop and the stop pin. The tool is calibrated or designed so that as long as there is a gap (i.e., second gap) a force being applied to the tissue by the tool is below a threshold or excessive level.

In a specific implementation, the travel of the handle is stopped (i.e., limited) when upper limit stop contacts or touches the stop pin. In another implementation, the travel of the handle is stopped when the handle contacts or touches a top surface of the extension below the handle. This top surface may be referred to as a travel limiting feature. In a specific implementation, the upper limit stop contacts the stop pin and a bottom surface of the handle contacts the top surface of the extension when a predetermined force is applied to the handle by the user. The predetermined force may range from about 57 grams (i.e., 2 ounces) to about 85 grams (i.e., 3 ounces).

The pressure control mechanism can provide a visual indication of the desirable levels or range of pressures or forces being applied to the tissue via the tool. Specifically, it can be difficult for the user to maintain a steady or constant pressure of the sensor unit or face of the sensor unit against the tissue. For example, the user's hand may lack the dexterity, the user's muscles may be tense, the user's hand may grow tired or become fatigued as the surgery progresses, the user may be nervous, and so forth. This can lead to tremors or "shaky" hands which can adversely affect the measurements. Applying excessive force can disturb the local perfusion, and therefore alter the tissue's actual oxygen saturation. Applying too little force can allow ambient light to slip between the pad and the tissue which can reduce signal quality.

This pressure control mechanism can help to ensure a constant pressure of the sensor unit against the tissue despite the variation in pressure applied to the tool or handle by the user. The pressure control mechanism may compensate for variation in pressure applied by the user. The pressure control mechanism can absorb excess levels of force to help ensure that the forces are not transmitted to the tissue being monitored. The pressure control mechanism can help ensure that a desirable pressure or force or range of desirable pressures or forces is applied against the tissue.

In this specific implementation, the handle is offset from the base via the extension. Typically, the extension is relatively stiff or rigid as compared to the spring. The spring is connected at a first end 459 of the handle. A bottom surface of the handle extending from the first end to a second end 462 of the handle, opposite the first end, extends without projecting over any sensor opening of the sensor unit. The second end of the handle is nearer the sensor unit than the first end of the handle. In this specific implementation, there are no structures such as the handle above a region of a top surface of the base where the sensor unit is directly below the region.

Figures 25, 26:
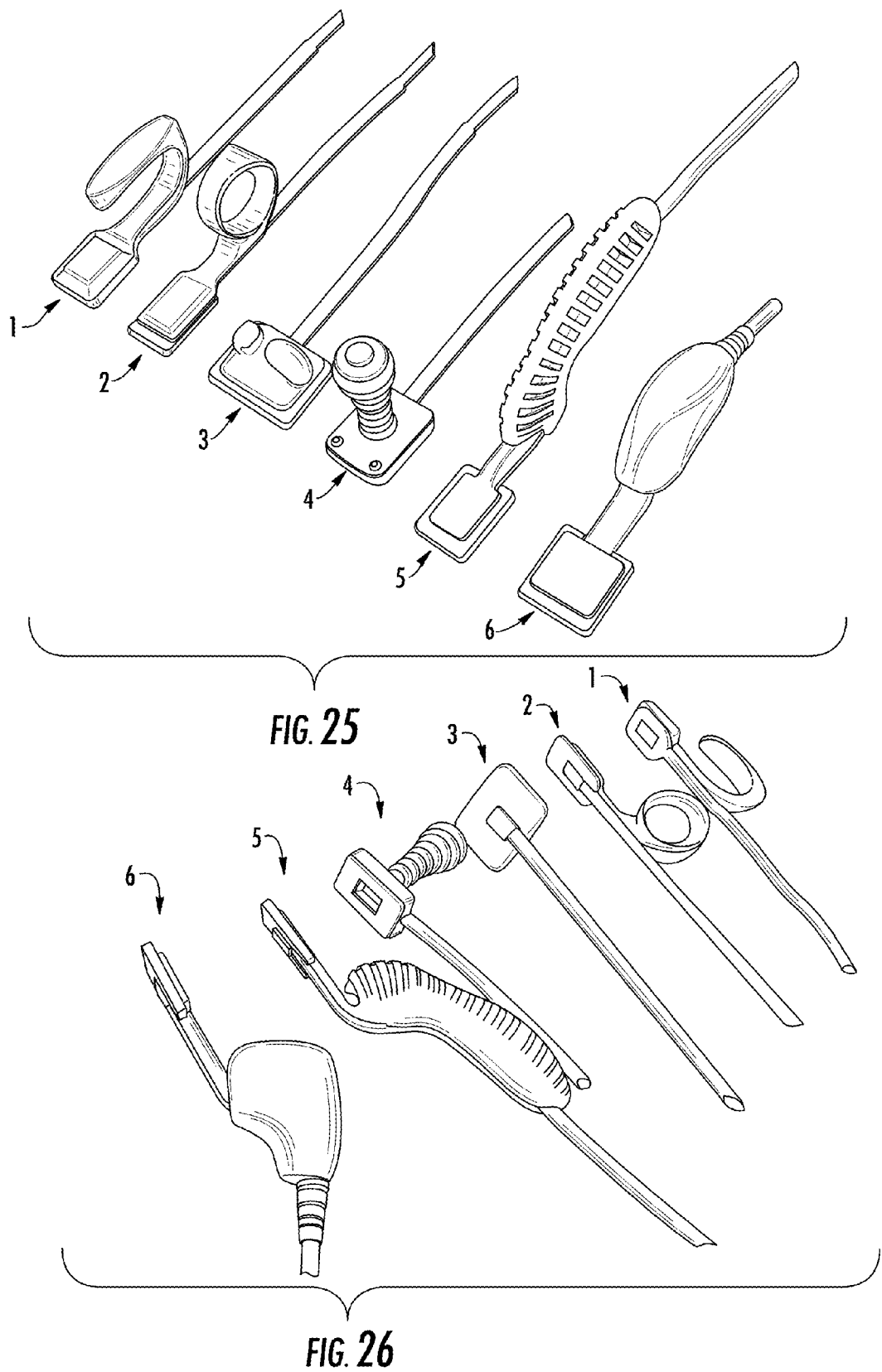
FIG. 25 shows perspective views of six alternative implementations of a tool.
FIG. 26 shows bottom views of the six alternative implementations.

Since there are no structures, such as the handle, above the base or sensor unit this results in a very low-profile design. This design allows the sensor unit to be positioned or slide into tight or confined areas where space is limited. A stud 426 to which the stop pin is connected may act as a stop or horizontal stop to indicate a depth within the tissue that the sensor unit can be inserted. In other implementations, the handle is directly above the base. For example, FIGS. 25-26 show a tool 4 having a handle directly above the base. FIGS. 27A-G show tool 4 in use.

In a specific implementation, a thickness or height of the base as measured from a tissue facing surface of the sensor unit to the top surface of the base is about 6 millimeters or less than 6 millimeters. The thickness can range from about 3 millimeters to about 12 millimeters. This includes, for example, 4, 5, 7, 8, 9, 10, 11, or 11.9 millimeters, or more than 12 millimeters. The thickness may be less than 3 millimeters.

In a specific implementation, a thickness of the pad in an uncompressed state is about 3 millimeters, but can range from about 1 millimeter to about 6 millimeters. This includes, for example, 1.5, 2, 2.5, 3.5, 4, 4.5, 5, 5.5, 5.9 millimeters, or more than 6 millimeters. The thickness may be less than 1 millimeter. A thickness of the sensor head or unit may be equal to or greater than the thickness of the pad in the uncompressed state. A thickness of the sensor head may be less than the thickness of the pad in the uncompressed state.

In a specific implementation, a thickness of the base measured without the pad is about 2 millimeters, but can range from about 0.5 millimeters to about 5 millimeters. This includes, for example, 1, 1.5, 1.6, 1.7, 1.8, 1.9, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.5, 4.9 millimeters, or more than 5 millimeters. The thickness may be less than 0.5 millimeters.

The region of the top surface of the base over the sensor unit openings may have a surface area that is equal to or greater than a surface area of the sensor unit. A distance from a distal edge 452 of the base to the stud may be about 27 millimeters, but can range from about 15 millimeters to about 40 millimeters. This includes, for example, 17, 19, 21, 22, 23, 24, 25, 26, 28, 29, 30, 31, 32, 33, 34, 35, 37, 39, 39.9 millimeters, or more than 40 millimeters. The distance may be less than 15 millimeters.

The extension includes a first end 453 and a second end 456, opposite the first end. The first end is connected to an end of the base or is supported by the base. The second end is unsupported by the base. That is, the extension is cantilevered relative to the base (i.e., having one end supported and an opposite end unsupported). The extension may be referred to as a platform.

Similarly, the handle includes first end 459 and a second end 462 opposite the first end. The second end of the handle is unsupported. The first end of the handle is supported via the spring. The spring is connected between the first end of the handle and the second end of the extension. The handle is cantilevered or is suspended over the extension, creating the first gap.

As shown in FIG. 4, this specific implementation of the gauge includes stud 426 which projects from a top surface of the base, opposite the bottom surface of the base. At an end of the stud is the stop pin which projects into or is received by the recess or limit region or travel limit region of the handle. The stop pin is fixed relative to the base and the recess is fixed relative to the handle. The handle is positioned between the stud and the spring.

In this specific implementation, the limit region is positioned at the first end of the handle. The limit region includes the pair of limit stops to limit a travel of the handle relative to the sensor unit. There is lower limit stop 463 at a bottom end of the limit region and upper limit stop 447 at a top end of the limit region, opposite the bottom end. The stop pin is between the upper and lower limit stops of the limit region. In this specific implementation, the limit region is a recess formed above the first gap and on a surface of the handle nearest the sensor unit. The recess is formed along a portion of a spine 465 of the handle which divides the tool into first and second halves or portions. The recess may be formed anywhere on the handle so long as the stop pin is able to project into the recess. The recess may be referred to as a notch, indentation, depression, or groove.

Note that the mechanical arrangement of the pressure control mechanism shown in FIG. 4 is merely an example of one particular implementation. In other implementations, other similar and equivalent elements and functions may be used or substituted in place of what is shown. For example, the recess or limit region is shown on the handle (or fixed relative to the handle) and the stop pin is shown on the base (or fixed relative to the base). However, these components can be swapped. The recess may be fixed relative to the base and the stop pin may be fixed relative to the handle.

As another example, the spring is shown near one end of the handle and the gauge (i.e., the stop pin and limit region) are shown near another opposite end of the handle. In the arrangement shown, a first distance between the sensor unit and spring is greater than a second distance between the sensor unit and the stop pin, limit region, or both. For example, the limit region or pair of limit stops is closer to the sensor unit than the spring.

However, the position of the spring can be swapped with the position of the stop pin and limit region so that the spring is closer to the sensor unit than the stop pin and the limit region. For example, spring is closer to the sensor unit than the limit region or pair of limit stops.

Although in this example the limit region has been implemented as a recess, the recess may be replaced with a pair of protrusions or bumpers extending from a surface of the handle. These protrusions can act as upper and lower limit stops for the stop pin to bump against.

A distance between the upper and lower limit stops is proportional to a distance that the handle can travel towards the sensor unit. Thus, spreading the upper and lower limit stops further apart allows the handle to travel further. The gauge may include markings or reference markings on the limit region that when aligned with the stop pin indicates the degree or distance that the handle has traveled. The markings may be color coded. For example, the upper limit stop or a region near the upper limit stop may be colored red to indicate that the desired maximum pressure has been reached or exceeded.

Figure 5:
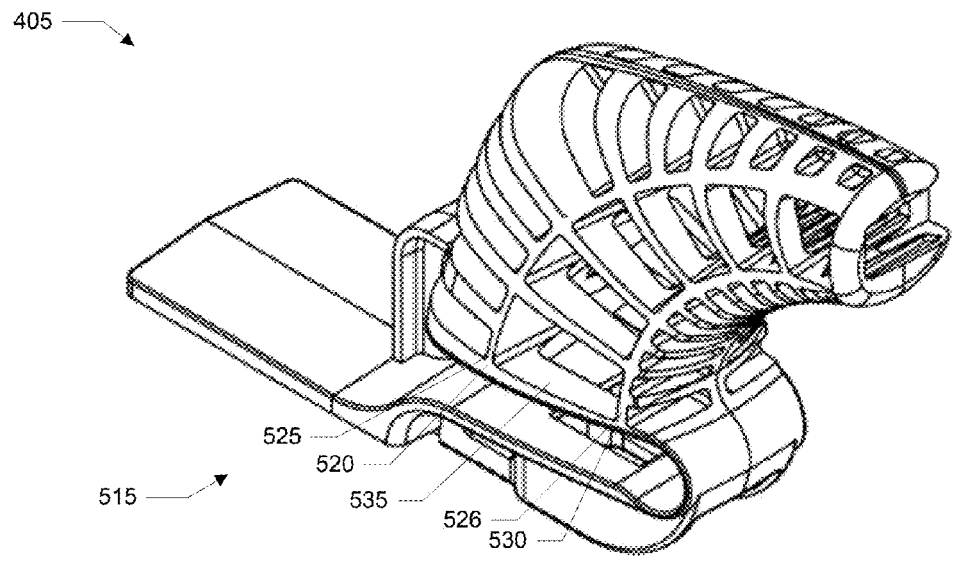
FIG. 5 shows a perspective view of the tool.

FIG. 5 shows a perspective view of tool 405 with the sensor unit omitted. The view is looking from a proximal end of the tool towards a distal end of the tool.

Figure 6:
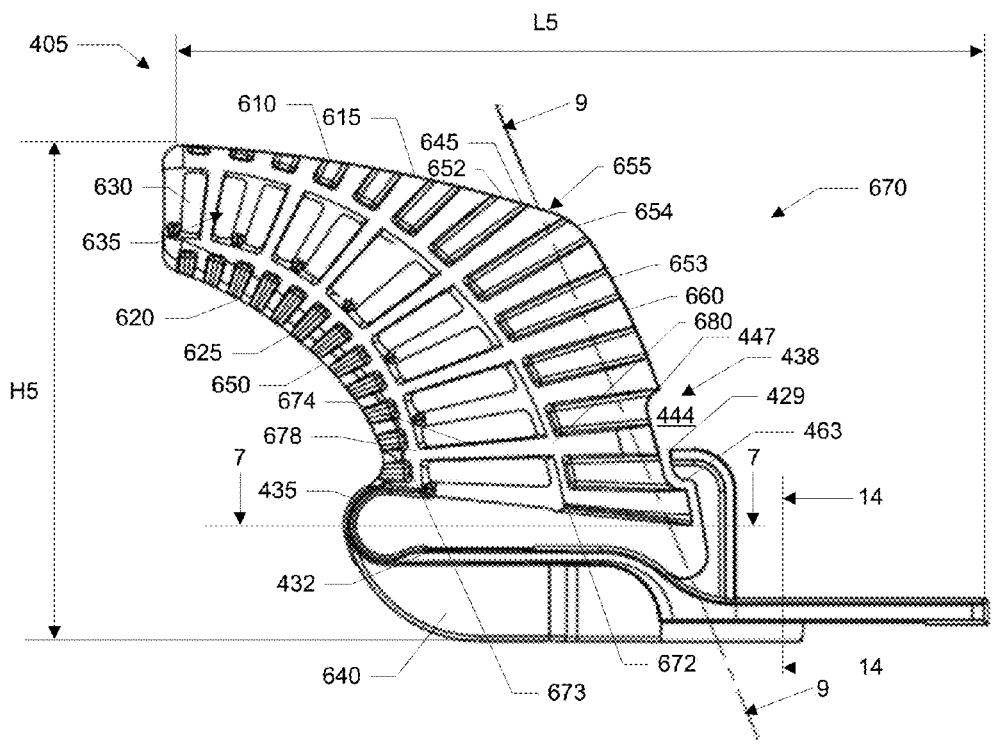
FIG. 6 shows a side view of the tool.
Figure 7:
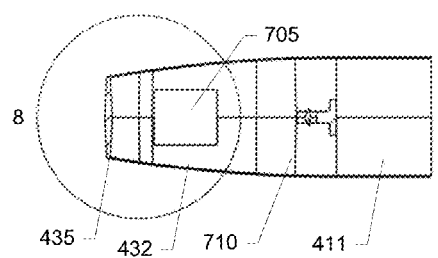
FIG. 7 shows a section view of the tool.
Figure 9:
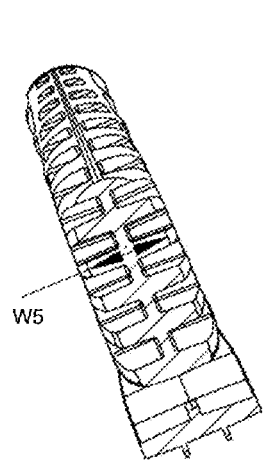
FIG. 9 shows a front view of the tool.
Figure 14:
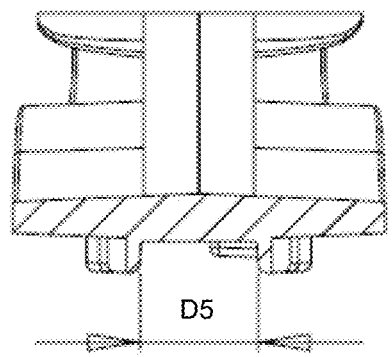
FIG. 14 shows another section view of the tool.

FIG. 6 shows a side view of tool 405. A dimension H5 indicates a height of the tool, a dimension L5 indicates a length of the tool. Section views 7-7, 9-9, and 14-14 are shown in FIGS. 7, 9, and 14, respectively.

In a specific implementation, spring 435 is designed to flex or bend when the user applies a force of about 42 grams (i.e., 1.5 ounces) to the handle. However, this force or threshold force can range from about 20 grams to about 200 grams. The force can range from about 0 grams (or ounces) to about 142 grams (i.e., 5 ounces). The force can range from about 57 grams (i.e., 2 ounces) to about 85 grams (i.e., 3 ounces). For example, the force can be about 15, 25, 30, 40, 45, 50, 55, 60, 65, 70, 80, 90, 100, 110, 120, 130, 140, 150, 160, 170, 180, 190, or 199 grams, or more than 200 grams. In an implementation, second gap 444 is closed (i.e., upper limit stop 447 and stop pin touch) when a force ranging from about 57 grams (i.e., 2 ounces) to about 85 grams (i.e., 3 ounces) is applied to the handle.

This wide-range of forces to close the second gap can address the different degrees of dexterity that different users may have. For example, some users may have very steady nerves. For these users, a spring having a lower stiffness may be desirable. Other users may have less dexterity and less sensitivity. For these other users, a spring having a higher stiffness may be desirable.

In a specific implementation, a desired user applied force to the handle is represented by a range of forces including a desired minimum force and a desired maximum force. The spring may be designed so that the desired user applied force is equal to or greater than the force required to initially deflect the spring from a first or precompressed condition to a second or further compressed condition. In the precompressed condition, a distance between lower limit stop 463 and stop pin 429 is less than a distance between upper limit stop 447 and the stop pin. For example, the distance may be zero where the lower limit stop and stop pin touch or contact.

In this specific implementation, the desired maximum force is that force just below the force required to compress the spring such that upper limit stop 447 contacts stop pin 429. The desired maximum force may be the force required to compress the spring such that the upper limit stop contacts the stop pin.

In this specific implementation, the user can feel the spring deflection or handle move when applying force to the handle. The user can see the travel of the handle as the spring deflects by observing the increasing distance between the lower limit stop and the stop pin as the user applies force to the handle or by observing the decreasing distance between the upper limit stop and the stop pin. As the lower limit stop is observed moving away from the stop pin, the user is given an indication that the desired minimum force has been reached or exceeded. As the upper limit stop approaches the stop pin, the user is given an indication that the maximum desired force is approaching. When the upper limit stop contacts the stop pin, the user is given an indication that the maximum desired force has been reached or exceeded.

Thus, the distance between the upper and lower limit stops can indicate the range of desired user applied forces. Within this range, the sensor unit is able to make accurate measurements. When the minimum force has been reached, there will be sufficient contact between the sensor unit or bottom surface of the base and the tissue. Specifically, for example, there will be no or little interference from ambient light; light from the source structures of the sensor unit will be able to properly pass into the tissue; and light from the tissue will be properly detected by the detector structures of the sensor unit.

In an implementation, the spring's flexibility is similar to that of hard rubber or soft plastic. The spring may have a type A durometer that ranges from about 70 to about 100. Typically, stiffness is the amount of force required to cause a unit of deformation or displacement and may be referred to as a spring constant.

In this specific implementation, the spring is made of plastic. Specifically, polypropylene homopolymer pro-fax 6523.

The spring is molded together or integrally as a single unit or unitary body with some of the other components of the tool such as the handle, base, stop pin, and extension. These components may all be formed from the same material. Making these components from the same material and same mold can help to reduce manufacturing costs.

Any process may be used to make the tool (e.g., injection molding). A colorant such as titanium dioxide bright white colorant may be added to make the tool white. One benefit of a white or light-colored tool is that it can provide a contrasting background for stains such as blood on the tool. This can indicate that caution should be taken when using the tool as the tool may have become contaminated with blood. For example, the blood may be blocking one or more of the sensor openings on the bottom surface of the base which may result in erroneous readings.

In another implementation, two or more of the components such as the spring and the handle are made separately such as by using separate molds. The components may then be connected together using any technique such as gluing or welding (e.g., plastic welding).

Generally, the spring can be made of any flexible, medical grade biocompatible plastic material. Some examples include medical grade polypropylene, polyethylene, and polyurethane. In other implementations, the spring is made of metal (e.g., steel, stainless steel, titanium, or copper). The spring and handle may be made of different materials. For example, the spring may be made of steel and the handle may be made of plastic.

Although FIG. 6 shows the spring positioned at an end of the first gap or handle, the spring may be positioned anywhere so long as it allows the handle to move, travel, pivot, or flex in response to pressure applied by the user. For example, the spring may be positioned between one end of the gap and an opposite end of the first gap. A spring may be positioned between the stop pin and the cable.

Further, although the figures show one spring, it should be appreciated that there can be more than one spring, such as two, three, or more than three springs. Each spring may have the same spring constant, stiffness, or force constant. Two or more springs may have different spring constants. There can be first and second springs connected between the handle and the base or sensor unit. A stiffness of the first spring may be the same or different from a stiffness of the second spring.

Figure 8:
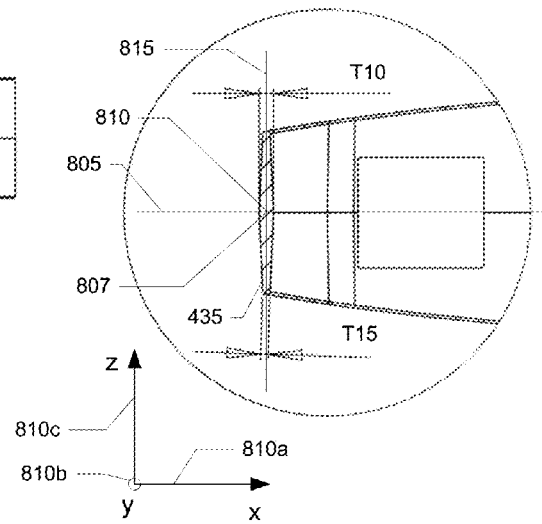
FIG. 8 shows an enlarged view of the section view shown in FIG. 7.

Other factors affecting spring stiffness may include the spring shape, dimensions, or both. For example, FIG. 7 shows section view 7-7 from FIG. 6. The section view is a top view which shows a cross section of spring 435 at second end 456 of extension 432. Circle 8 refers to a detailed view of the second end of the extension which is shown in FIG. 8. Extension 432 includes an opening 705. The extension is connected via a ramp 710 to base 411. The ramp is at an incline relative to the base and is at a decline relative to the extension. In other words, from the extension to the base the ramp slopes down; from the base to the extension the ramp slopes up.

Referring now to FIG. 8, the spring at its middle has a first thickness T10 and at its opposite ends a second thickness T15. A line 805 parallel to an x-axis 810*a* passes through a center (or reference point) 807 of the spring. Line 805 divides the tool longitudinally. A line 810 parallel to a y-axis 810*b* which projects out of the page passes through center 807 and is perpendicular to line 805. A line 815 parallel to a z-axis 810*c* passes through center 807 and is perpendicular to lines 805 and 810.

When a force is applied to the handle, the spring flexes or bends about line 815 and the handle rotates or pivots about line 815. The stiffness of the spring and thus the amount of force used to bend the spring is proportional to the thickness of the spring. Thus, increasing the first thickness, second thickness, or both can increase the amount of force used to bend the spring. Conversely, decreasing the first thickness, second thickness, or both can decrease the amount of force used to bend the spring.

In a specific implementation, first thickness T10 is about 1.3 millimeters (i.e., 0.05 inches), but can range from about 0.5 millimeters to about 5 millimeters. This includes, for example, 0.6, 0.7, 0.8, 0.9, 1, 1.1, 1.2, 1.4, 1.5, 1.6, 1.7, 1.8, 1.9, 2, 2.1, 2.2, 2.3, 2.4, 2.5, 2.6, 2.7, 2.8, 2.9, 3, 4, or 4.9 millimeters, or more than 5 millimeters. The first thickness may be less than 0.5 millimeters.

The thickness of the spring tapers from a middle portion of the spring and outwards towards the opposite ends of the spring. In other words, in this specific implementation, there is a gradual diminution of thickness as one moves from the middle portion of the spring and outwards towards the ends of the spring. Thus, second thickness T15 is less than first thickness T10. In a specific implementation, second thickness T15 is about 0.8 millimeters (i.e., 0.03 inches), but can range from about 0.1 millimeters to about 3 millimeters. This includes, for example, 0.2, 0.3, 0.4, 0.5, 0.6, 0.7, 0.8, 0.9, 1, 1.1, 1.2, 1.4, 1.5, 1.6, 1.7, 1.8, 1.9, 2, 2.1, 2.2, 2.3, 2.4, 2.5, 2.6, 2.7, 2.8, or 2.9 millimeters, or more than 3 millimeters. The second thickness may be less than 0.1 millimeters.

As shown in FIG. 8, in this specific implementation, spring 435 has a cross-sectional shape of a lozenge or diamond. In other words, the cross-sectional shape has four equal sides and two acute angles and two obtuse angles. The two acute angles are opposite each other. The two obtuse angles are opposite each other. The spring is oriented so that line 805 bisects the two obtuse angles and line 815 bisects the two acute angles.

This shape and orientation of the spring may be used to facilitate the assembly of the tool. For example, in a specific implementation, when the tool is removed from the mold the tool is in an unassembled state. In the unassembled state, the sensor unit, cable, and pad are not yet attached. The handle may be oriented such that the limit region or recess on the handle and the stop pin are not yet engaged. To assemble the tool, the manufacturer can grasp the base and handle, twist the handle about line 810 so that the bottom end of the recess can slip below the stop pin (see FIG. 4), push the handle down towards the base thus bending the spring about line 815, and then release the handle to allow the spring to untwist so that the bottom end of the recess slips below the stop pin. Having the thickness at the opposite ends of the spring being less than the thickness in the middle of the spring can facilitate the twisting of the spring about line 810 during assembly.

Although FIG. 8 shows the spring having a diamond-shaped cross section, a spring can have any cross-sectional shape such as a rectangle, square, triangle, circle, oval, ellipse, and so forth.

In a specific implementation, the spring is formed as a c-shaped spring or a flat strip spring. However, any type of spring may be used. Some examples of spring types include tension or extension springs, compression springs, torsion springs, coil or helical springs, conical springs, balance springs, and leaf springs (i.e., laminated or carriage spring). The spring may be referred to as a flexible strip or resisting member (e.g., force-resisting member).

In a specific implementation, the spring is implemented as a living hinge. Such a hinge may be a thin flexible hinge made from plastic that joins two rigid plastic parts together (e.g., base and handle), allowing them to bend along the line of the hinge. The living hinge may be manufactured in an injection molding operation that creates all three parts at one time as a single part. The living hinge may be made from a resin such as polyethylene or polypropylene.

Referring now to FIG. 6, the handle includes an upper set of valleys 610 and ridges 615, a lower set of valleys 620 and ridges 625, a first channel 630 between the upper and lower sets of valleys and ridges, and a set of openings 635 along the first channel. There is a second channel 640 below extension 432. The handle further includes an upper spine 645 and a lower spine 650.

One or more components of the tool such as the handle may be designed to be not or minimally reflective. This can help ensure that more of the light which is transmitted into the tissue is received back at the detectors, instead of being reflected off the tool. For example, a surface of the tool may be coated with an antireflective material (such as a black oxide coating) to make it less reflective than the original starting material. One or more surface portions of the tool may be colored (e.g., black flat color), or finished (e.g., matte finish), or textured (e.g., bead-blasted finish) to reduce reflectivity. Another benefit of reducing reflectivity is that there will be less glare for the surgeon and other medical people during the operation.

One or more components of the tool may be made of a transparent, semi-transparent, or opaque material. In a specific implementation, the cord or portions of the cord within the handle are visible (FIG. 4). The cord or portions of the cord are exposed via openings 635 (FIG. 6). The cord or portions of the cord may instead or additionally be exposed through a transparent or semi-transparent material.

In a specific implementation, openings 635 include a first set of openings on a first side of the handle and a second set of openings on a second side of the handle, opposite the first side. In this specific implementation, the first and second sets of openings are offset or are shifted from each other. That is, an opening of the first set of openings is not aligned with an opening of the second set of openings. A first opening of the first set of openings overlaps a portion of a second opening of the second set of openings and a portion of a third opening of the second set of openings. Offsetting the openings can make the handle stronger as compared to a handle where the openings are not offset or are aligned. Offsetting the openings can make the handle more resistant to bending as compared to a handle where the openings are aligned. In another implementation, the first and second sets of openings are aligned with each other.

An opening may be bounded by two opposite walls of the first channel and a pair of struts extending between the two opposite walls of the first channel. A strut on one side of the handle may be offset from a strut on an opposite side of the handle. For example, in a specific implementation, (as shown in FIGS. 5 and 6) on a first side 515 of the handle (FIG. 5) there is a first reference point 520 on a first wall 525 of the first channel and a second reference point 526 on a second wall 530 of the first channel. A first strut 535 extends between the first and second reference points. On a second side 670 of the handle (FIG. 6) there is a third reference point 672 on the first wall of the first channel and a fourth reference 673 point on the second wall of the first channel. The third and fourth reference points are directly opposite the first and second reference points. In this specific implementation, a second strut 674 does not extend between the third and fourth reference points. Rather, on the second side of the handle there is a fifth reference point 678 above fourth reference point 673 and a sixth reference point 680 above third reference point 672. The second strut extends between fifth reference point 678 and sixth reference point 680.

The upper and lower spines extend perpendicularly outward from the channel and generally curve arcuately away from the base and towards a proximal end of the handle. A height of a portion of the upper spine as measured from the first channel may progressively decrease as one moves towards the proximal end of the handle.

The upper spine bisects the upper set of valleys and ridges. In a specific implementation, the upper spine includes a first slope 652 and a second slope 653 which meet at a transition point 654. The second slope is between the first slope and the limit region or recess. The second slope is steeper than the first slope.

The lower spine bisects the lower set of valleys and ridges. A height of the upper spine may be different from a height of the lower spine. In this specific implementation, the height of the upper spine is greater than the height of the lower spine. In other implementations, the height of the upper spine is less than the height of the lower spine. The heights of the upper and lower spines are the same. The spines can help make the handle rigid.

In this specific implementation, the ridges and valleys are alternating. There is a ridge which is followed by an adjacent valley. A thickness of the ridge may be the same as a thickness of the adjacent valley. A thickness of a first ridge or valley is the same as a thickness of a second ridge or valley. In another implementation, the thickness of the ridge is different from the thickness of the adjacent valley or nonadjacent valley. Two or more ridges may have different thicknesses. Two or more valleys may have different thicknesses.

The valleys and ridges and openings 635 can help improve the user's grip on the handle so that the tool does not accidentally slip from the user's hand. For example, fluids such as blood are typically present during surgical procedures. The blood may be mixed with fat cells or other debris and tissue which can coat the various surgical tools making the tools slippery. The valleys can help draw the blood away from the surface of the handle by providing a place for the blood to collect so that the handle does not become slippery with fluids.

The valley and ridge feature and openings 635 also helps to reduce the weight of the handle as compared to a solid handle and can make the tool easier to hold. This can be desirable during long surgical procedures where the user must hold the tool for an extended period of time. These features can also facilitate the manufacture of the handle by making the tool easier to mold. Further, because of these features less material is required to make the handle which lowers manufacturing costs.

A surface 655 of the handle may include ergonomic features such as textures, knurls (i.e., a series of small ridges or beads), or both to aid in gripping. In this specific implementation, the handle is designed to be gripped or pinched on its opposite sides between the user's thumb and middle finger while the forefinger or index finger rests on a front surface 660 (or a portion of the front surface).

In this specific implementation, the front surface is above limit region 438 and is between a first side of the handle and a second side of the handle, opposite the first side. The front surface may be planar or flat to provide a comfortable resting place for the user's forefinger. In another implementation, the front surface is curved such as curved concave to provide a depression in which the user's forefinger can rest. The front surface may be curved convex.

FIG. 9 shows section view 9-9 from FIG. 6. A dimension W5 indicates a width of the front surface. In a specific implementation, W5 is about 14.5 millimeters (i.e., 0.57 inches), but can range from about 10 millimeters to about 20 millimeters. This includes, for example, 11, 12, 13.1, 13.2, 13.3, 13.4, 13.5, 13.6, 13.7, 13.8, 13.9, 14, 14.1, 14.2, 14.3, 14.4, 14.6, 14.7, 14.8, 14.9, 15, 15.1, 15.2, 15.3, 15.4, 15.5, 15.6, 15.7, 15.8, 15.9, 16, 17, 18, 19, 19.9 millimeters, or more than 20 millimeters. Width W5 may be less than 10 millimeters.

Figure 10:
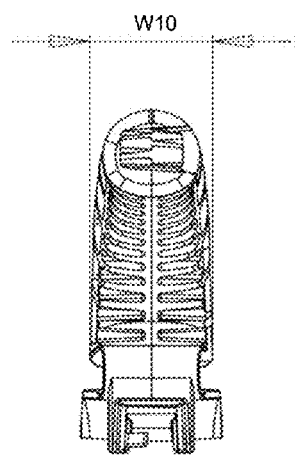
FIG. 10 shows a rear view of the tool.
Figure 11:
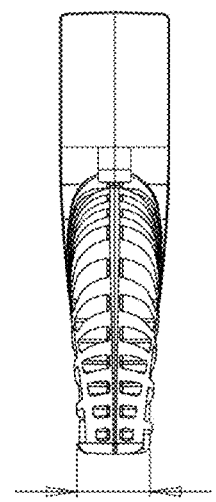
FIG. 11 shows a top view of the tool.

FIGS. 10 and 11 show rear and top views, respectively of the handle. As shown in FIGS. 10 and 11, the handle's width or a portion of the handle's width may taper. For example, as shown in FIG. 10, the width of the bottom portion of the handle may be constant. Thereafter, as shown in FIG. 11, the width of the top portion of the handle may vary. A dimension W10 indicates a first width of the bottom portion of the handle (FIG. 10). A dimension W15 indicates a second width of the top portion of the handle (FIG. 11). The top portion of the handle tapers from the first width to the second width. The tapering of the handle can make the handle comfortable to hold.

In a specific implementation, width W10 is about 18.5 millimeters (i.e., 0.73 inches), but can range from about 10 millimeters to about 25 millimeters. This includes, for example, 11, 12, 13, 14, 15, 16, 16.5, 17, 17.5, 18, 19, 19.5, 20, 21, 22, 23, 24, or 24.9 millimeters, or more than 25 millimeters. Width W10 may be less than 10 millimeters. Width W15 is about 14.2 millimeters (i.e., 0.56 inches), but can range from about 7 millimeters to about 20 millimeters. This includes, for example, 8, 9, 10, 11, 12, 12.5, 13, 13.5, 14, 14.5, 15, 15.5, 16, 16.5, 17, 18, 19, or 19.9 millimeters, or more than 20 millimeters. Width W15 may be less than 7 millimeters.

Figure 13:
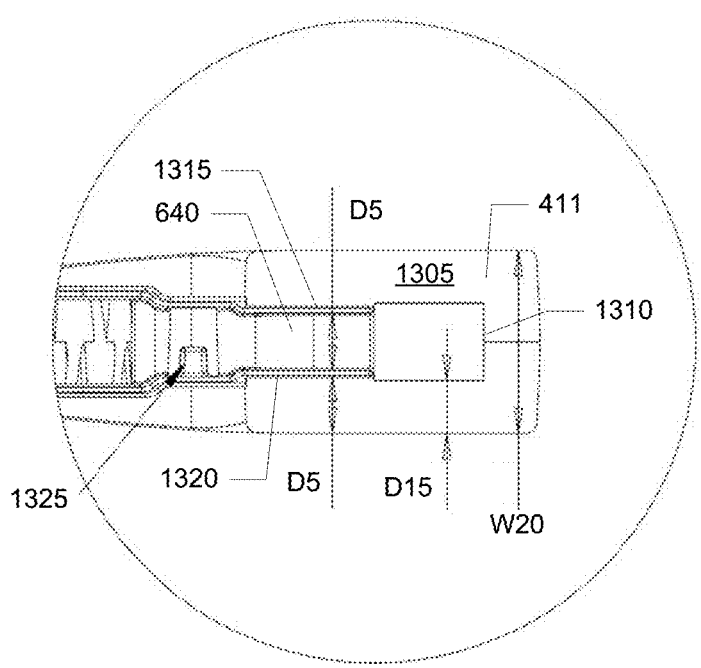
FIG. 13 shows an enlarged bottom view of the tool shown in FIG. 12.

The size of the tool such as its height H5 (FIG. 6), length L5 (FIG. 6), and width of the base W20 (FIG. 13) may vary greatly depending upon the application, the user's preference, or both. In a specific implementation, height H5 is about 50.1 millimeters (i.e., 2.05 inches), but can range from about 30 millimeters to about 75 millimeters. This includes, for example, 35, 40, 45, 50, 55, 60, 65, 70, or 74.9 millimeters, or more than 75 millimeters. Height H5 may be less than 30 millimeters.

Length L5 is about 82.6 millimeters (i.e., 3.25 inches), but can range from about 50 millimeters to about 150 millimeters. This includes, for example, 60, 70, 80, 90, 100, 110, 120, 130, 140, or 149 millimeters, or more than 150 millimeters. Length L5 may be less than 50 millimeters.

Width W20 is about 21.3 millimeters (i.e., 0.84 inches), but can range from about 10 millimeters to about 50 millimeters. This includes, for example, 15, 20, 25, 30, 35, 40, 45, or 49 millimeters, or more than 50 millimeters. Width W20 may be less than 10 millimeters.

Figure 12:
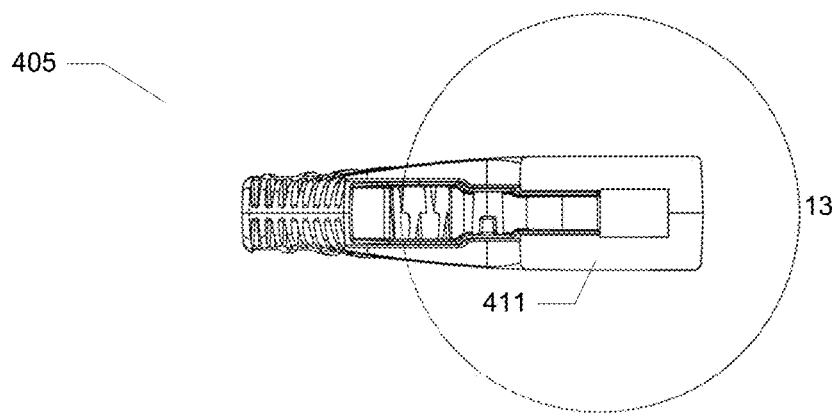
FIG. 12 shows a bottom view of the tool.

FIG. 12 shows a bottom view of tool 405. Circle 13 refers to a detailed view shown in FIG. 13. Base 411 includes a bottom surface 1305. A portion of second channel 640 extends onto the bottom surface of the base. An outline 1310 indicates the position of the sensor unit attached to the bottom surface of the base.

Second channel 640 includes a first wall 1315 and a second wall 1320, opposite the first wall. The first and second walls extend perpendicularly away from the bottom surface of the base. The walls begin at a proximal edge of the outline of the sensor unit, extend past the bottom surface of the base, and terminate at the spring (see FIG. 6). A tab 1325 extends from one of the walls in a direction parallel to the bottom surface and towards the other wall.

The second channel and tab help to secure and guide the sensor unit cable. For example, when the tool is assembled the sensor unit cable is routed through the second channel and slipped below the tab. In this specific implementation, the tab terminates before reaching the other wall. This provides a space between the tab and the other wall so that the cable can be placed in the space and slipped beneath the tab. The cable is placed so that it is between the first and second channel walls.

In this specific implementation, the second channel is positioned equidistant from two opposite edges of the base. In other implementations, the channel is placed offset from a centerline passing longitudinally through the base. For example, the distance between the first wall of the channel and a first edge of the base may be different from a distance between the second wall of the channel and a second edge of the base, opposite the first edge of the base.

In a specific implementation, a distance D5 from one wall to a nearest edge or edge of the base is about 6.8 millimeters (i.e., 0.27 inches), but can vary greatly. A distance D10 indicates a distance between the first and second walls. See also FIG. 14. In a specific implementation, distance D10 is about 6.8 millimeters (i.e., 0.27 inches), but can vary greatly. Distance D10, D5, or both may vary proportionally with a width of the cable. A distance D15 indicates a distance from an edge of the outline for the sensor unit to a side edge of the base. In a specific implementation, distance D15 is about 6.1 millimeters (i.e., 0.24 inches), but can vary greatly.

The routing of the sensor unit cable is shown in FIG. 4. The cable passes through the first channel and along a portion of the extension, into opening 750 of the extension (FIG. 7), across the first gap, into the first channel, and then exits the proximal end of the handle. This routing can help to improve cable strain resistance. It should be appreciated that the cable may be routed different from what is shown in FIG. 4. For example, the cable may be routed so that it is on top of the surface of the handle instead of being routed through the channel.

Figure 15:
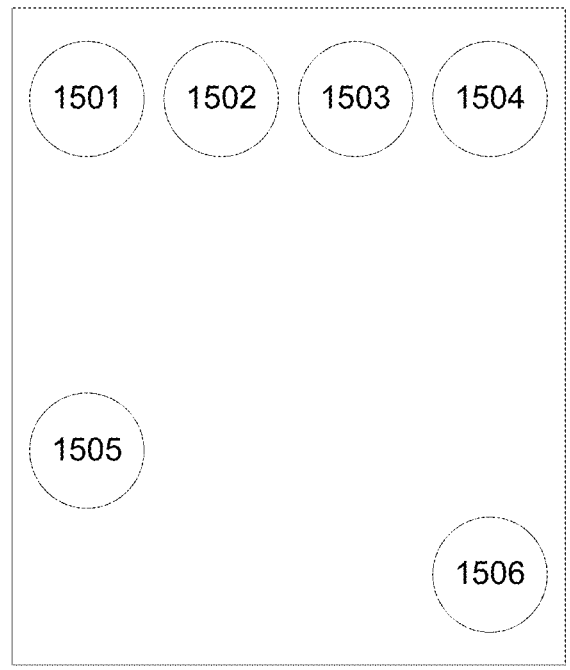
FIGS. 15-22 show various source and detector opening arrangements of the tool.

FIG. 15 shows a specific implementation of a sensor unit. Such a sensor unit may be incorporated in the various probe implementations (e.g., tool 305 or 405) discussed above in this application.

This sensor has six openings 1501-1506. Openings 1501-1504 are arranged in a line closer to a first edge of the sensor, while openings 1505 and 1506 are arranged closer to a second edge, which is opposite the first edge. In fact, opening 1506 is closer than opening 1505 to the second edge. These openings are for sources and detectors, and there can be any number of sources, any number of detectors, and they can be in any combination. In an implementation of a sensor head, the first edge is distal to the second edge, which is closer to a cable attached to the probe or hand holding the probe.

In one implementation, openings 1501-1504 are detectors while openings 1505 and 1506 are sources. However, in other implementations, there can be one or more detectors, two or more detectors, one or more sources, or two or more sources. For example, there may be three detectors and three sources or one detector and five sources.

In FIG. 15, the openings are positioned asymmetrically such that a line drawn through openings 1501-1504 is not parallel to a line drawn through openings 1505 and 1506. However, a line drawn through openings 1501 and 1505 is parallel to a line through openings 1504 and 1506. Additionally, the distance between openings 1501 and 1504 is shorter than the distance between openings 1505 and 1506.

Thus, the distance between openings 1501 and 1505 does not equal the distance between openings 1501 and 1506; the distance between openings 1502 and 1505 does not equal the distance between openings 1503 and 1505; and the distance between openings 1503 and 1505 does not equal the distance between openings 1504 and 1506.

In this implementation, the sensor unit has a rectangular shape, but the sensor unit may have any shape such a trapezoid, triangle, dodecagon, octagon, hexagon, square, circle, or ellipse. A sensor of any shape or form can incorporate the sensor openings in the pattern shown and described.

In a specific implementation, a distance between openings 1501 and 1504 is five millimeters. A distance between each of the openings 1501, 1502, 1503, and 1504 is 5/3 millimeters. A distance between 1501 and 1505 is five millimeters. A diameter of an opening is one millimeter.

Figure 16:
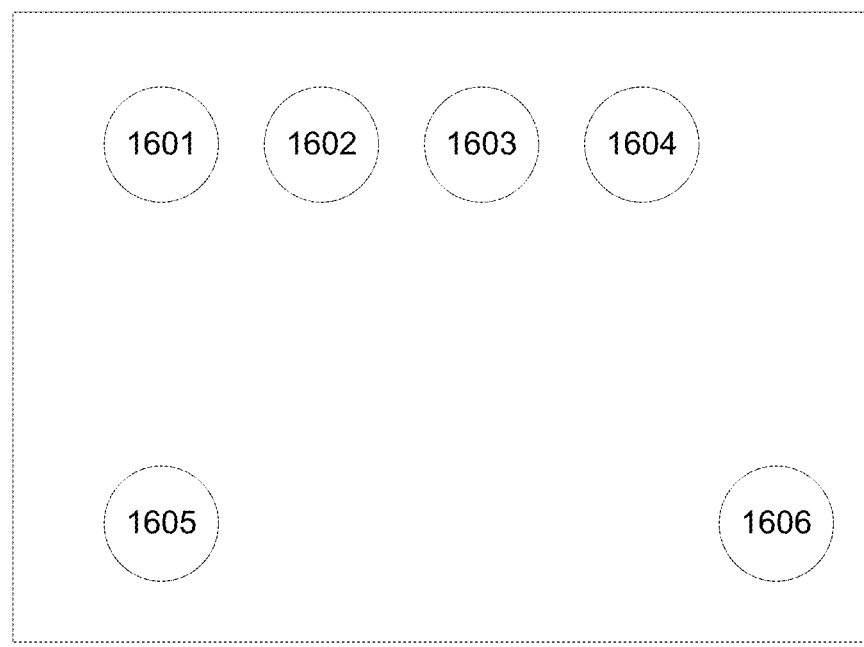

FIG. 16 shows a variation of the implementation of the sensor unit shown in FIG. 15. The sensor unit in this specific implementation is also arranged to include six openings 1601-1606. Similar to FIG. 15, openings 1601-1604 are arranged in a line closer to a first edge of the sensor, while openings 1605 and 1606 are arranged closer to a second edge, which is opposite the first edge. In one implementation, openings 1601-1604 are detectors while openings 1605 and 1606 are sources.

In this figure, the openings are positioned so that a line drawn through openings 1601-1604 is parallel to a line through openings 1605 and 1606. However, a line drawn through openings 1601 and 1605 is not parallel to a line through openings 1604 and 1606.

Additionally, similar to FIG. 15, the distance between openings 1601 and 1604 is shorter than the distance between openings 1605 and 1606. Thus, the distance between openings 1601 and 1605 does not equal the distance between openings 1601 and 1606; the distance between openings 1602 and 1605 does not equal the distance between openings 1603 and 1605; and the distance between openings 1603 and 1605 does not equal the distance between openings 1604 and 1606.

In this implementation, the sensor unit itself is of a greater area relative to the area of the sensor unit shown in FIG. 15. In another implementation, the sensor unit may be of a smaller area relative to the area shown in FIG. 15. In yet another implementation, the sensor unit may be of a greater area relative to that shown in FIG. 16.

Further, in a specific implementation, the openings are the same size as each other (e.g., each opening has the same diameter or each opening has the same area). A specific implementation uses one-millimeter circular openings. However, in another implementation, the diameter of one opening may be different from other openings, or there may be some openings with different diameters than other openings. There can be any combination of differently sized openings on one sensor unit. For example, there are two openings with a C size and other openings have a D size, where C and D are different and D is greater than C. Also, openings are not necessarily circular. So, C and D may represent area values.

Figure 17:
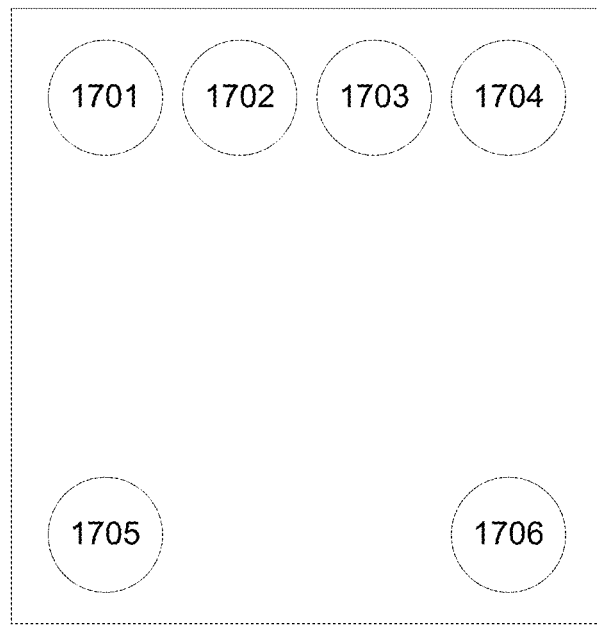

FIG. 17 shows another variation of the implementation of the sensor unit shown in FIG. 15. The sensor unit in this specific implementation is also arranged to include six openings 1701-1706. Similar to FIGS. 15 and 16, openings 1701-1704 are arranged in a line closer to a first edge of the sensor, while openings 1705 and 1706 are arranged closer to a second edge, which is opposite to the first edge. In one implementation, openings 1701-1704 are detectors while openings 1705 and 1706 are sources.

In this figure, the openings are positioned so that a line drawn through openings 1701-1704 is parallel to a line through openings 1705 and 1706. In fact, these two lines are equal in length. Furthermore, a line drawn through openings 1701 and 1705 is parallel (and equal in length) to a line through openings 1704 and 1706.

Thus, in this specific implementation, the distance between openings 1701 and 1706 is equal to the distance between openings 1704 and 1705. This specific arrangement includes further equalities: the distance between openings 1702 and 1705 equals that between openings 1703 and 1706 and the distance between openings 1703 and 1705 equals that between openings 1702 and 1706.

In an implementation, the distances between openings 1701-1704, 1704-1706, 1706-1705, and 1705-1701 are all equal; thus, in this implementation openings 1701, 1704, 1706, and 1705 form the vertices of a square. In other implementations, however, four openings may form the vertices of any quadrilateral, such as a rectangle, a rhombus, a trapezoid, or a parallelogram.

Aside from the equalities mentioned, the distances between each of the openings 1701-1704 and each of the openings 1705-1706 are not equal. For instance, the distance between openings 1701 and 1705 does not equal the distance between openings 1701 and 1706.

Figure 18:
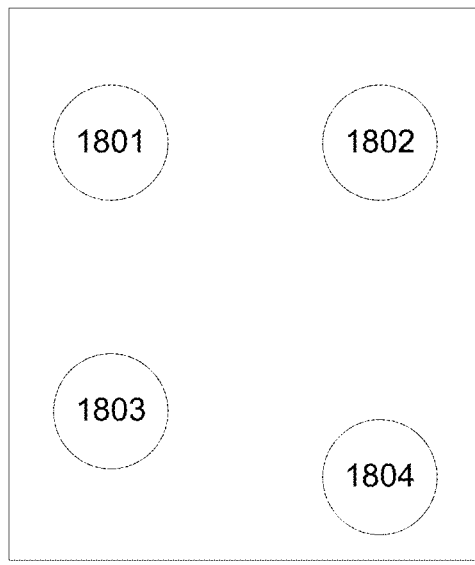

FIG. 18 shows a specific implementation of a sensor unit which is arranged to include four openings 1801-1804. Openings 1801 and 1802 are arranged in a line closer to a first edge of the sensor, while openings 1803 and 1804 are arranged closer to a second edge, which is opposite the first edge. In fact, opening 1804 is closer than opening 1803 to the second edge. In an implementation the first edge is distal to the second edge, which is closer to a cable attached to the probe or hand holding the probe.

In one implementation, openings 1801 and 1802 are detectors and openings 1803 and 1804 are sources. However, in other implementations, there can be one or more detectors, two or more detectors, one or more sources, or two or more sources. For example, there may be three detectors and one source or one detector and three sources.

In FIG. 18, the openings are positioned asymmetrically such that a line drawn through openings 1801 and 1802 is not parallel to a line through openings 1803 and 1804. However, a line drawn through openings 1801 and 1803 is parallel to a line through openings 1802 and 1804.

Additionally, the distance between openings 1801 and 1802 is shorter than the distance between openings 1803 and 1804. Thus, in FIG. 18, the distance between openings 1801 and 1803 does not equal the distance between openings 1802 and 1804 and the distance between openings 1802 and 1803 does not equal that between openings 1802 and 1804.

Figure 19:
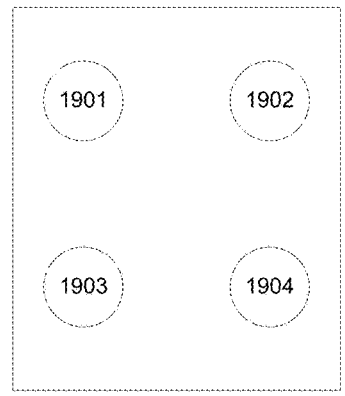

FIG. 19 shows a variation of the implementation of the sensor unit shown in FIG. 18. The sensor unit of this implementation also includes four openings 1901-1904. Openings 1901 and 1902 are arranged in a line closer to a first edge of the sensor, while openings 1903 and 1904 are arranged closer to a second edge, which is opposite the first edge. In one implementation, openings 1901 and 1902 are detectors and openings 1903 and 1904 are sources.

In FIG. 19, the openings are positioned symmetrically such that a line drawn through openings 1901 and 1902 is parallel, and equal, to a line through openings 1903 and 1904. Additionally, a line drawn through openings 1901 and 1903 is parallel, and equal, to a line through openings 1902 and 1904.

In an implementation, the distances between openings 1901-1902, 1902-1904, 1904-1903, and 1903-1901 are all equal; thus, in this implementation openings 1901, 1902, 1903, and 1904 form the vertices of a square. In other implementations, however, four openings may form the vertices of any quadrilateral, such as a rectangle, a rhombus, a trapezoid, or a parallelogram.

Some of the distances between the centers of particular openings are unequal; for instance, the distance between openings 1901 and 1903 does not equal the distance between openings 1901 and 1904.

Figure 20:
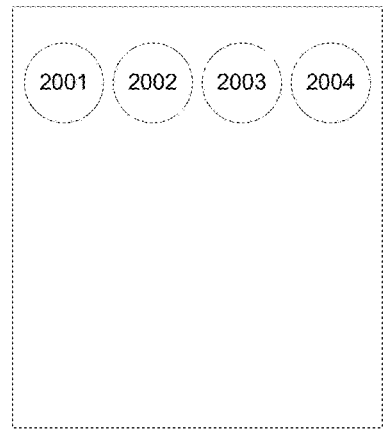

FIG. 20 shows another variation of the implementation of the sensor unit shown in FIG. 18. Similar to FIGS. 18 and 19, this specific implementation of a sensor unit includes four openings 2001-2004.

However, in this variation, all four of the openings are arranged in a line closer to a first edge of the sensor. Specifically, in this figure, openings 2001-2004 lie in a row parallel to the first edge so that a straight line may be drawn through each opening. In one implementation, openings 2001 and 2002 are detectors and openings 2003 and 2004 are sources.

In this specific implementation, the distance between openings 2001 and 2002 is equal to the distance between openings 2002 and 2003; this distance is also equal to that between openings 2003 and 2004.

Additionally, the distance between openings 2001 and 2003 equals that between openings 2002 and 2004. In fact, this distance is twice the distance between each individual opening. Thus, the distance between openings 2001 and 2003 does not equal that between openings 2001 and 2002; the former is twice the distance of the latter.

Figure 21:
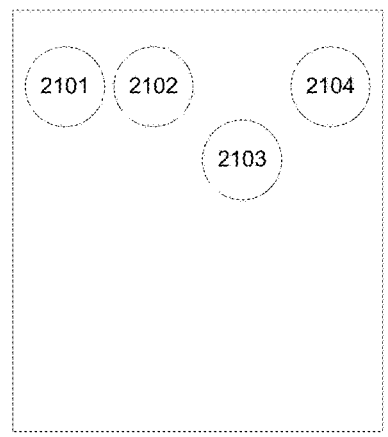

FIG. 21 shows a variation of the implementation of the sensor unit shown in FIG. 20. This implementation of a sensor unit is similarly arranged to include four openings 2101-2104. Also, this arrangement of openings is located closer to a first edge of the sensor. However, in this figure, openings 2101, 2102, and 2104 lie in a row parallel to the first edge so that a straight line may be drawn through the center of each opening, while opening 2103 lies below that straight line.

In this implementation, opening 2103 lies equally spaced between openings 2102 and 2104; in other implementations, opening 2103 can lie closer to one opening than another. In one implementation, openings 2101 and 2102 are detectors and openings 2103 and 2104 are sources.

In this specific implementation, as mentioned above, the distance between openings 2102 and 2103 equals that between openings 2103 and 2104. Aside from this equality, the distances between the openings are unequal. For example, in this implementation, the distance between openings 2101 and 2103 does not equal the distance between openings 2102 and 2104 and the distance between openings 2102 and 2103 does not equal that between openings 2102 and 2104.

Figure 22:
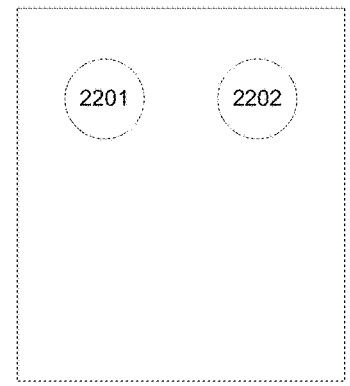

FIG. 22 shows a specific implementation of a sensor unit which is arranged to include two openings 2201 and 2202. Similar to FIGS. 20 and 21, this arrangement of openings is located closer to a first edge of the sensor. Additionally, openings 2201 and 2202 lie in a row parallel to the first edge so that a straight line may be drawn through each opening. In one implementation, opening 2201 is a detector and opening 2202 is a source.

Although we have shown sensor units with two, four, and six openings in these figures, other implementations may include different numbers of sensor openings. For instance, there may be three, five, seven, eight, or more than eight openings.

Although the openings are shown as circles, an opening can have any shape, including obround, oblong, oval, ellipse, square, rectangle, triangle, or other shapes. A sensor unit can include openings having different shapes such as an opening having one shape (e.g., circle) and another opening having a different shape (e.g., square).

There may be any combination of detectors and sources and the number of detectors need not equal the number of sources. For instance, if there are three openings, there may be one detector and two sources or two detectors and one source. As another example, if there are eight openings, there may be two detectors and six sources, five detectors and three sources, or four detectors and four sources.

Further, one or more sensor openings may be covered with a film such as a light-transparent film, a semitranslucent film, or a light diffusing film. Such a film can help attenuate the light back-reflected from the tissue. The sensor openings may be covered with a protective cover, sleeve, or barrier. In this specific implementation, light from the sensor openings can pass through the protective cover and into the tissue. Light from the tissue can pass through the protective cover and be detected by the detector structures. The protective cover can be removed and a new protective cover can be placed on the tool for a next use or next patient.

In a specific implementation, a sensor arrangement includes a first source structure, a second source structure, a first detector structure that includes optical fiber, and a second detector structure. A first distance extends between the first source structure and the first detector structure without touching another source or detector structure. A second distance extends between the second source structure and the second detector structure without touching another source or detector structure. A third distance extends between the second source structure and the first detector structure without touching another source or detector structure. A fourth distance extends between the first source structure and the second detector structure without touching another source or detector structure. The first distance is different from the second and third distances. The second distance is different from the third distance.

In various implementations, the fourth distance is different from the first, second, and third distances. There are no source or detector structures between the first and second source structures. There are no source or detector structures between the first source structure and the first detector structure. The first source structure and first detector structure have the same cross-sectional area. A fifth distance between the first and second source structures is greater than a sixth distance between the first and second detector structures.

In implementations discussed so far in this application, each opening on the bottom surface of the base or sensor unit has a single fiber associated with it. However, in further implementations of the invention, each opening may have multiple fibers—two or more—associated with it. Or, each opening of the probe may have multiple light paths or light channels associated with it.

These light paths can be used simultaneously for transmitting to tissue or receiving light from tissue. Within a single opening, there may be two source structures, two detector structures, or one source and one detector structure. And for a single tool, probe, or sensor unit of the tool, there may be two or more such openings with multiple light channels.

The bottom surface of the base may include one opening having a concentric core fiber with an inner core light channel which is surrounded by an outer core light channel. In a specific implementation, the inner core light channel is a source channel and the outer core light channel is a detector channel. However, in another implementation, the inner core light channel is a detector channel and the outer core light channel is a source channel. Furthermore, in another implementation, the inner and outer core light channels may not be concentric. For example, the inner and outer core light channels may not share the same centers. Openings having two or more fibers are further discussed in U.S. patent application Ser. No. 12/194,508, filed Aug. 19, 2008, which is incorporated by reference.

Source and detector arrangements are further discussed in U.S. Pat. No. 7,355,688, issued Apr. 8, 2008; U.S. Pat. No. 7,525,647, issued Apr. 28, 2009; and U.S. Pat. No. 7,538,865, issued May 26, 2009; and U.S. patent application Ser. No. 12/126,860, filed May 24, 2008; Ser. No. 12/194,508, filed Aug. 19, 2008; and Ser. No. 12/359,792, filed Jan. 26, 2009 which are incorporated by reference along with all other references cited in this application.

In a specific implementation, the sensor openings for the source and detector arrangements are part of a sensor unit. The sensor unit is a separate part or component. In another implementation, the sensor openings are formed directly on the base itself or a portion of the base. Optical wires (e.g., fiber optic cables) may be routed through the tool and directly connected to the individual sensor openings on the base itself. A beam combiner may be included in the console as discussed in U.S. Pat. No. 7,355,688.

Figures 23, 24:
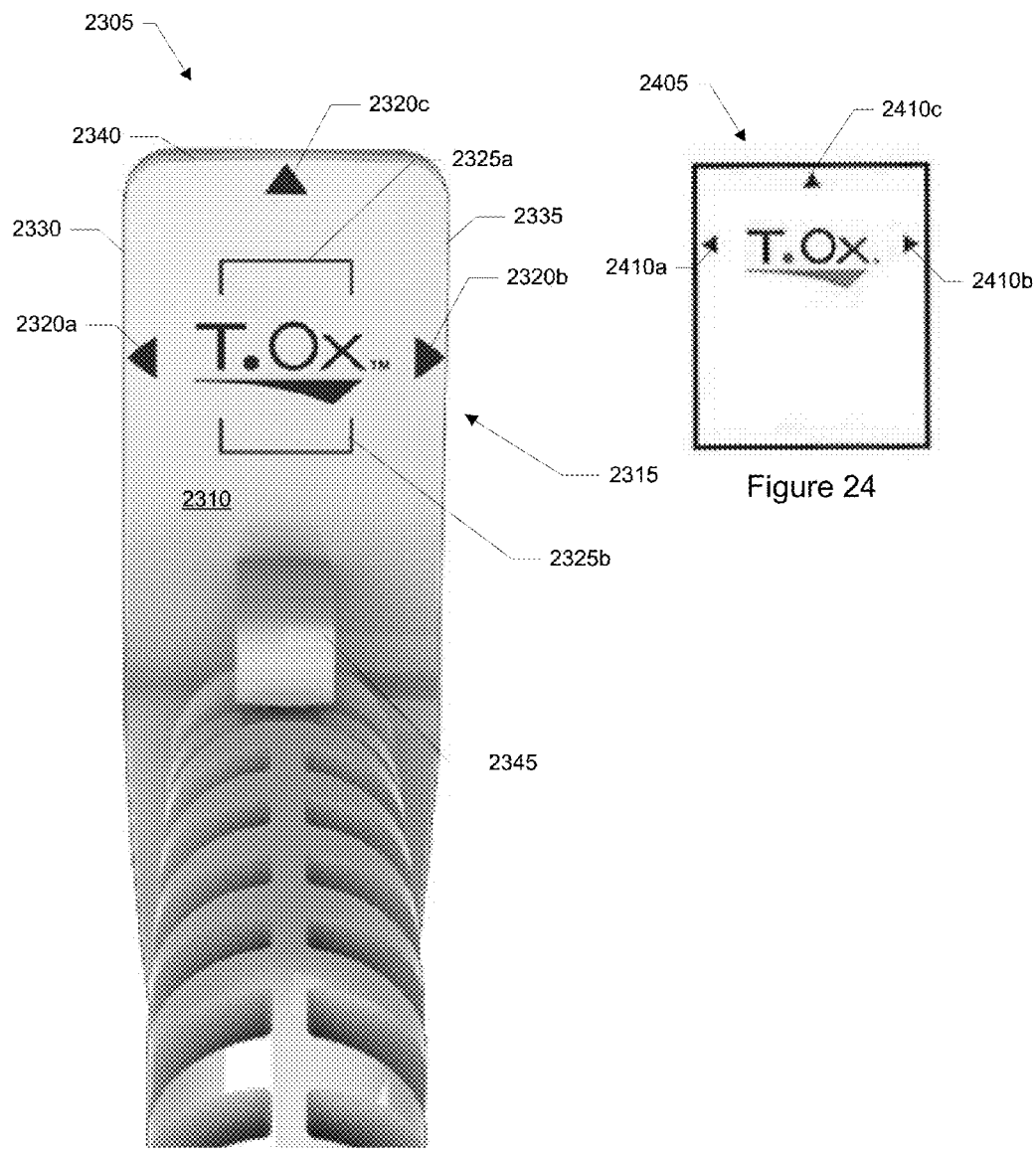
FIG. 23 shows a top view of a tool having a specific implementation of indicator markings.
FIG. 24 shows a top view of a tool having another specific implementation of indicator markings.

FIG. 23 shows a top view of a specific implementation of a tool 2305. A top surface 2310 of the base includes a set of markings, indicators, or visual indicators 2315. The set of markings includes first, second, and third arrows 2320a-c, and first and second brackets 2325a-b.

First arrow 2320a points towards a left-hand side edge 2330 of the base. Second arrow 2320b points towards a right-hand side edge 2335 of the base, opposite the left-hand side edge. Third arrow 2320c points towards a top edge 2340 of the base which joins the left and right-hand side edges.

The arrows can be located or positioned anywhere along the edges of the base. In a specific implementation, the first and second arrows are located at about a midpoint between the top edge of the base and a stop pin 2345. A distance from the top edge of the base to the first arrow is equal to a distance from the stop pin to the first arrow. Similarly, a distance from the top edge of the base to the second arrow is equal to a distance from the stop pin to the first arrow. The third arrow is located at a midpoint of the top edge or between the left and right-hand side edges. A distance from the left-hand side edge to the third arrow is equal to a distance from the right-hand side edge to the third arrow.

The brackets or square brackets can be located anywhere on the top surface of the base. In this specific implementation, the brackets are located below or behind the third arrow. The second bracket is a mirror image of the first bracket. The brackets are located at a midpoint between first and second arrows.

The brackets indicate a position of the sensor unit attached to the bottom surface of the base with respect to the top surface of the base. The brackets indicate an outline or at least a portion of the outline of the sensor unit. The first bracket indicates a top portion of an outline of the sensor unit. The second bracket indicates a bottom portion of the outline of the sensor unit.

The arrows serve as a reference point so that the tool can be removed from a location on the tissue and then later repositioned at that same location and orientation. This allows repeatable readings or measurements to be made. For example, the user can position the tool over the tissue to be measured. Using a surgical marking pen, the user can make marks or dots on the tissue or skin such that each dot is aligned with one of the first, second, or third arrows. The tool can then be removed and later repositioned at the same location by aligning or matching the dots and the arrows. In a specific implementation, if one were to draw a cross through the dots (e.g., the three dots corresponding to the three arrows), the intersection would indicate the center of the sensor unit.

In an implementation, a method for using the tool includes placing the sensor unit over a tissue to be measured. The sensor unit is placed on the tissue such that it is over a specific location on the tissue and is in a specific orientation with respect to the tissue. The method includes making at least one dot (e.g., mark) on skin adjacent, near, or next to the tissue to be measured. The at least one dot corresponds to or is aligned with at least one visual indicator on the tool. The skin may surround, border, or at least partially surround or border the tissue to be measured. The tool can then be removed from the tissue and repositioned over the specific location on the tissue and in the specific orientation. This can be done by positioning the tool on the tissue such that the at least one dot on the skin is aligned with the at least one visual indicator on the tool.

In another implementation, the at least one dot may be made on the tissue to be measured (e.g., on skin above the tissue to be measured). For example, the tool may include a hole passing from the top surface of the base to the bottom surface of the base. In this specific implementation, the user can mark the skin above the tissue to be measured by passing a tip of a surgical pen through the hole and marking the skin. The tool can be repositioned by aligning the mark on the skin with the hole.

The arrows, brackets, or both can help in assisting or aiding the user (e.g., surgeon) to determine the active region of the sensor unit so that the sensor unit can be aligned over the tissue or region of interest to be measured.

The markings may be made using any technique for making a visible impression on the tool including, but not limited to, printing, silkscreen printing, masking, stamping, plating, thermography, embossing, painting, engraving, etching, anodizing, oxidizing, deposition, imprinting, and chemical processing. The marking may be made anywhere on the tool such as the top surface of the base as shown in the figure, a side surface of the base which joins the top and bottom surfaces of the base, or both. The marking may be a bump or notch that is perceptible by touch. However, it is generally desirable that the marking is visible while looking down towards the top surface of the tool.

FIG. 24 shows a top view of a base of a tool 2405 having indicator arrows and no brackets. There are first, second, and third arrows 2410a-c, respectively. The first arrow points towards a first side edge of the base. The second arrow points towards a second side edge of the base, opposite the first side edge. The third arrow points towards a top edge of the base, between the first and second side edges. That is, the top edge joins the first and second side edges.

In a specific implementation, a first plane passing through the first and second arrows divides a bottom surface of the base into first and second regions. In this specific implementation, the first region has detector structures and no source structures. The second region has source structures and no detector structures. The second region is closer to the handle than the first region. In another implementation, the first region is closer to the handle than the second region.

In another implementation, a second plane passes through the third arrow and intersects or is perpendicular to the first plane. The second plane divides the bottom surface of the base into third and fourth regions. In this specific implementation, the third region has at least one detector structure and at least one source structure. The fourth region has at least one detector structure and at least one source structure. A number of detector structures in the third region may be equal to or different from a number of detector structures in the fourth region. A number of source structures in the third region may be equal to or different from a number of source structures in the fourth region. A region can have detector structures and no source structures. A region can have source structures and no detector structures. A number of detector structures in a region may be less than, equal to, or greater than a number of source structures in the region.

In this specific implementation, a distance from the top edge of the base to the first and second arrows is about a quarter of the length of the base from the top edge to the bottom edge of the base.

In some implementations, there are no markings. There can be arrow indicators and no bracket indicators such as shown in FIG. 24. There can be bracket indicators and no arrow indicators. Further, the bracket and arrow indicators are merely some specific examples of visual indicators. Other examples or types of visual indicators, graphics, or symbols including letters, characters, numbers, words, lines, pictures, images, icons, shapes (e.g., triangles), and so forth.

FIGS. 25-26 show top and bottom views, respectively, of six alternative designs for the tool. In alternative designs 1-2 and 5-6, the handle does not project over the base. In alternative design 1, the tool is formed as a c-shape. The handle is formed as a hook. The handle extends over the extension and there is a gap below the handle or between the handle and the extension. In alternative design 2, the handle is formed as a hoop, loop, or circle. The extension is the spring which connects the base and the handle. In this specific implementation, the spring is tangent to the handle. In alternative design 5, the handle is formed as an elongated member with a textured surface. The handle is connected to the base via an extension which acts as a spring. A distal end of the handle includes a stop, indicator, or protrusion which contacts the spring to limit a travel of the handle. In alternative design 6, the handle has a smooth surface.

In alternative design 3, a handle includes a pair of ring sections. There is a pad having a cavity to hold a sensor unit, a base connected to the pad and positioned over the cavity, a first ring section extending from a surface of the plate, and a second ring section. The second ring section is a mirror image of the first ring section. The first and second ring sections define an opening to receive a user's finger. When the opening receives the finger a portion of the finger is above the sensor unit. In this specific implementation, ends of the first and second ring sections do not touch. In another implementation, the ends of the first and second ring sections touch to define a closed circle or ring.

In alternative design 4, there is a bottom base layer having an opening, a top base layer, a handle connected to the top base layer, and a pad having a cavity. The pad is connected between the bottom and top base layers. The opening overlaps at least a portion of the cavity. The pad is more compliant than the bottom and top base layers. Applying a threshold level of force to the handle causes at least a portion of the pad to be compressed between the bottom and top base layers. A surface of the handle is textured. The texturing includes a set of concentric circles or groves around the handle which extend from one end of the handle to an opposite end of the handle. The handle is formed as an elongated bulb-shaped part which makes the handle comfortable to hold. In this specific implementation, the cable is not routed through the handle.

FIGS. 27A-G show alternative design 4 and a method of using the tool. In a specific implementation, the tool includes a pair of gambrels or posts extending through a pair of openings in the top base layer. An area of an opening in the pair of openings is greater than a cross-sectional area of a gambrel. Thus, a portion of the pad is visible from the top base layer through the pair of openings.

In this specific implementation, the tool may be used by pushing the handle forwards, sideways, or diagonally to ensure sufficient contact between the bottom base layer and the tissue. As the handle is pushed or pulled, the top base layer tilts with respect to the bottom base layer as portions of the pad are compressed. In other words, the bottom base layer remains in sufficient contact with the tissue as the handle is pushed or pulled such that light does not escape from the cavity (or only a small amount of light escapes) and ambient light does not enter the cavity (or only a small amount of ambient light enters).

A position of the pair of gambrels relative to the pair of openings can provide an indication of the pressure being applied to the tissue. For example, the position of a gambrel within an opening may indicate excessive pressure is being applied to the tissue such as when the gambrel touches or contacts an edge of the opening. The position of the gambrel within an opening may indicate an uneven pressure is being applied to the tissue such as when one gambrel within one opening is at a position different from another gambrel within another opening.

Referring now to FIG. 6, a representative flow for making tool 405 is described in steps 1 to 5 below.

1. Provide the tool, the tool being in an unassembled state.
2. Assemble the pressure control mechanism of the tool.
3. Route the sensor unit cable through the tool.
4. Attach the sensor unit that is at a first end of the cable to the bottom surface of the base.
5. Attach the pad to the bottom surface of the base.
6. Attach a connector to a second end of the cable, opposite the first end.

Although the steps above are listed in a specific order, the steps may take place in any order, as desired and depending on the specific application. There may be additional or other steps, which may replace one or more of the above steps. Certain steps may be repeated. Certain steps may be omitted. For example, step 2 may be omitted where a mold for the tool allows the tool to be produced such that the pressure control mechanism is assembled (i.e., the stop pin is aligned within the recess of the handle).

In step 1 of the flow, the tool is provided in an unassembled state. The tool may be provided using any type of manufacturing process such as injection molding. In injection molding, a material (e.g. plastic granules) is forced into a mold cavity where it cools and hardens to the configuration of the mold cavity. The tool is then removed from the cavity. Colorants may be added during the molding process.

In a specific implementation, the mold includes first, second, and third cavities. The first cavity is connected to the second cavity and the second cavity is connected to the third cavity. The first cavity is for producing the tool base or base portion. The second cavity is for producing the spring portion. The third cavity is for producing the handle portion. Material such as plastic is injected into the mold where it cools and hardens to the configuration of the mold cavities. When the material or product is removed from the mold, there is then a single piece of material or product that includes the base, spring, and handle portions.

In step 2, the pressure control mechanism is assembled. This step may include substeps a-b below.

a. Twist the spring by twisting the handle relative to the base and push the two pieces together.

b. Release one of the handle or the base allowing the spring to untwist with another one of the handle or the base such that the stop pin is aligned within the recess of the handle.

In step 3, the sensor unit cable is routed through the tool. The cable or a portion of the cable may be further secured to the tool via an adhesive such epoxy or glue.

In step 4, the sensor unit which is at a first end of the cable is attached to the bottom surface of the base. The sensor unit may be positioned on the bottom surface by butting a proximal side edge of the sensor unit against the ends of the channel walls and aligning opposite side edges of the sensor unit with opposite channel walls, the proximal side edge being between the opposite side edges of the sensor unit. The sensor unit is attached to the bottom surface of the base such that the source and detector openings of the sensor unit face away from the bottom surface of the base.

The sensor unit may be secured to the bottom surface of the base via an adhesive such as epoxy which cures into a resin or any other type of adhesive or glue. Some examples of resins include thermosetting resins, polyester resins, amino resins, polyamide resins, polyvinyl butyral resins, acrylic resins, phenol formaldehyde resins, ketone formaldehyde resins, and alkyd resins.

In step 5, the pad is placed so that it at least partially around the sensor unit. For example, the sensor unit may be bordered on at least three sides by pad material. A side of the pad may be coated with an adhesive (e.g., pressure sensitive adhesive) so that the pad may be secured to the bottom surface of the base. The pad may be referred to as a light shield pad. The pad may include a reflective layer or material that surrounds or at least partially surrounds the sensor unit. The reflective layer may be a foil, mirror, or any other material or coating that reflects light. The reflective layer can help prevent source light from escaping, reduce ambient light, or both. The pad can help form a seal between the tissue and the tool (i.e., the base portion of the tool).

In a specific implementation, a thickness of the pad in an uncompressed state is less than a thickness of the sensor unit. A portion of the sensor unit may extend past a surface of the pad. In another implementation, the thickness of the pad in the uncompressed state is the same as the thickness of the sensor unit. The sensor unit and the surface of the pad may be coplanar. In another implementation, the thickness of the pad in the uncompressed state is less than the thickness of the sensor unit.

In step 6, attach a connector to a second end of the cable, opposite the first end. In a specific implementation, the connector is attached to the end or second end of the cable after the cable is routed through the tool. If the connector were attached before the cable was routed through the tool it might not be possible to route the cable through the tool because of the size of the connector. Generally, the cable is routed through the tool before attaching the sensor unit, connector, or both to an end of the cable.

An instruction sheet describing how to use the tool may be packaged or included with the tool. In a specific implementation, the instructions include a diagram or figure of the tool showing a side view of the tool and a diagram or figure showing a top view of the tool and the reference points for location marking. The instructions may further include the following steps:

1. Grasp the handle and gently apply the sensor face to the tissue. Do not allow the handle to bottom out against the base as this means that excessive force has been applied.

2. Maintain a pressure-limiting gap as shown (in the figure). Applying excessive force will disturb the local perfusion, and therefore alter the tissue's actual oxygen saturation.

3. To obtain repeatable readings in multiple locations, mark each exact location and orientation of the sensor on the skin with a sterile surgical marking pen using the reference points provided. Pause the console while changing locations.

4. Keep sensor and pad dry and free of blood. Do not allow holes on sensor face to become obstructed. The sensor head is surrounded by a light shield pad, however, excessive ambient light may reduce signal quality.

The instruction sheet may further include information that specifies an expiration date (e.g., a "use by date"), a serial number, size (e.g., length and width) of the sensor unit, base, or both.

Figures A-U in an appendix of parent U.S. patent application Ser. No. 12/623,945 show various implementations for markings on the top surface of the base of the tool. Figures V-X show various views of a specific embodiment of the tool. Figures Y-Z show the operation of the pressure limiting gap for a specific embodiment of the tool. Figure AA shows an example of an instruction sheet that may be included with the tool.

In a specific implementation, the tool is designed to be disposable, such as after one use. In another implementation, the tool is designed to be reusable. In this specific implementation, a disposable transparent sleeve or cover may be slipped over at least a portion of the base to help protect the base from being contaminated. Afterwards, disposable transparent sleeve may be disposed and the tool itself can be reused by slipping a new disposable transparent sleeve over the base.

As discussed above, in various implementations, measurements are made while the user holds the sensor unit via the handle against the tissue to be measured. In specific implementations, the bottom surface of the base which faces the tissue does not have any adhesives since the sensor unit is being held against the tissue by the user. In other words, a portion of the bottom surface which surrounds or at least partially surrounds the sensor openings has no adhesives. There is no release liner on the bottom surface.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A method comprising:
providing an oximeter device comprising a sensor head comprising a probe face that faces a tissue to be measured and a handle;
on the probe face, forming first, second, and third sensor structures;
positioning the second sensor structure at a first distance from the first sensor structure;
positioning the third sensor structure at a second distance from the first sensor structure, wherein the first distance is different from the second distance; and
providing an elastic member comprising a spring constant coupled between the sensor head and handle.

2. The method of claim 1 wherein the first sensor structure comprises a source structure and the second and the third sensor structures comprise detector structures.

3. The method of claim 1 wherein the first sensor structure comprises a detector structure and the second and the third sensor structures comprise source structures.

4. The method of claim 1 wherein the first and second sensor structures are positioned to form a first line, the first and third sensor openings are positioned to form a second line, and the first line is not parallel to the second line.

5. The method of claim 1 wherein the first, second, and third sensor structures are arranged in a line.

6. The method of claim 1 comprising:
providing a pressure sensor on the sensor head.

7. The method of claim 1 comprising:
coupling a light emitting diode to the first sensor structure;
coupling a photodetector to the second sensor structure; and
coupling a battery coupled to the light emitting diode and the photodetector.

8. The method of claim 1 wherein a first line passes through the base portion, in a first direction that is transverse to the bottom surface of the base portion,
a second line extends in the first direction and intersects a surface of the handle,
the first line passes through the first sensor structure,
the first line does not pass through the handle, and
a first distance is between the first line and the second line in a second direction, transverse to the first direction, wherein the first distance is greater than about 1 millimeter.

9. The method of claim 1 comprising:
coupling a light emitting diode to the first sensor structure;
coupling a photodetector to the second sensor structure; and
coupling a battery coupled to the light emitting diode and the photodetector,
wherein a first line passes through the base portion, in a first direction that is transverse to the bottom surface of the base portion,
a second line extends in the first direction and intersects a surface of the handle,
the first line passes through the first sensor structure,
the first line does not pass through the handle, and
a first distance is between the first line and the second line in a second direction, transverse to the first direction, wherein the first distance is at least about 1 millimeter.

10. The method of claim 1 wherein the oximeter device is a tissue oximeter probe.

11. A method comprising:
providing an oximeter device comprising a probe face that will face a tissue to be measured and a handle;
forming at least one sensor structure on the probe face;
providing a pressure sensor at a sensor head, wherein the sensor head comprises the probe face; and
coupling an elastic member comprising a spring constant between the sensor head and the handle.

12. The method of claim 11 comprising:
using the pressure sensor, detecting a pressure being applied to the tissue by the probe face.

13. The method of claim 11 comprising:
coupling a battery to the pressure sensor.

14. The method of claim 11 comprising:
coupling a light emitting diode to a first sensor structure formed on the bottom surface of the base portion; and
coupling a photodiode to a second sensor structure formed on the probe face.

15. The method of claim 11 wherein the oximeter device is a tissue oximeter probe.

16. A method comprising:
providing an oximeter device comprising a probe face that faces a tissue to be measured and a handle;
forming a first sensor structure and a second sensor structure on the probe face;
coupling a light emitting diode to the first sensor structure;
coupling a photodiode to the second sensor structure;
coupling a battery to the light emitting diode and the photodetector; and
coupling a flexible member comprising a spring constant between the probe face and the handle.

17. The method of claim 16 wherein the battery supplies power to the light emitting diode and the photodetector, and the method comprises:
coupling a recharger circuit to the battery, wherein the recharger circuit recharges the battery.

18. The method of claim 16 wherein a first line passes through the base portion, in a first direction that is transverse to the bottom surface of the base portion,
a second line extends in the first direction and intersects a surface of the handle,
the first line passes through the first sensor structure,
the first line does not pass through the handle, and
a first distance is between the first line and the second line in a second direction, transverse to the first direction, wherein the first distance is at least about 1 millimeter.

19. The method of claim 16 comprising:
coupling a processing circuit to the light emitting diode, photodetector, and battery.

20. The method of claim 16 comprising:
coupling a processing circuit to the light emitting diode, photodetector, and battery; and
a display, coupled to the processing circuit.

21. The method of claim 16 wherein the handle comprises:
a proximal end;
a distal end, closer to the base portion than the proximal end;
a front side, wherein the front side comprises a first portion from the proximal end to a first bend having a first slope, and a second portion from the first bend to the distal end having a second slope; and
a back side that is opposite the front side.

22. The method of claim 21 wherein the second slope is steeper than the first slope.

23. The method of claim 16 wherein a first line passes through the first sensor structure and a second line passes through an axis of the handle, and the first line and second line are angled with respect to each other.

24. The method of claim 16 wherein at least a first portion of the handle is adapted to be cradled in an area between a thumb and forefinger of a user's hand.

25. The method of claim 24 wherein at least a second portion of the handle is adapted to be contacted by the forefinger of the user's hand, and the second portion of the handle is on a different side of the handle to the first portion of the handle.

26. The method of claim 16 comprising:
forming a third sensor structure on the probe face,
positioning the second sensor structure at a first distance from the first sensor structure;
positioning the third sensor structure at a second distance from the first sensor structure, wherein the first distance is different from the second distance,
wherein at least a first portion of the handle is adapted to be cradled in an area between a thumb and forefinger of a user's hand.

27. The method of claim 16 wherein the oximeter device is a tissue oximeter probe.

* * * * *